US 9,744,066 B2

United States Patent
Kazerooni et al.

(10) Patent No.: US 9,744,066 B2
(45) Date of Patent: *Aug. 29, 2017

(54) TRUNK SUPPORTING EXOSKELETON AND METHOD OF USE

(71) Applicant: THE REGENTS OF THE UNIVERSITY OF CALIFORNIA, Oakland, CA (US)

(72) Inventors: Homayoon Kazerooni, Berkeley, CA (US); Erich Hacker, Portland, OR (US); Lee-Huang Chen, Anaheim, CA (US); Wayne Tung, Berkeley, CA (US); Nathan Poon, Oakland, CA (US); Theerapat Yangyuenthanasan, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/944,635

(22) Filed: Nov. 18, 2015

(65) Prior Publication Data
US 2016/0206498 A1    Jul. 21, 2016

Related U.S. Application Data

(63) Continuation-in-part of application No. 14/125,117, filed as application No. PCT/US2012/041891 on Jun. 11, 2012.
(Continued)

(51) Int. Cl.
*A61F 5/02* (2006.01)
*A61H 1/02* (2006.01)
*A61F 5/01* (2006.01)

(52) U.S. Cl.
CPC ............. *A61F 5/026* (2013.01); *A61F 5/028* (2013.01); *A61H 1/0244* (2013.01);
(Continued)

(58) Field of Classification Search
CPC ............... A61H 1/0292; A61H 1/0244; A61H 2201/165; A61H 2201/1652; A61F 5/026; A61F 5/028
See application file for complete search history.

(56) References Cited

U.S. PATENT DOCUMENTS 1,202,851 A   10/1916  Kelly
1,409,326 A    3/1922  Williamson
(Continued)

FOREIGN PATENT DOCUMENTS

CN   201934433 U    8/2011
JP    01274758 A   11/1989
(Continued)

OTHER PUBLICATIONS

International Search Report issued in a corresponding Application No. PCT/US2015/061284 dated Apr. 11, 2016.

*Primary Examiner* — Justine Yu
*Assistant Examiner* — Timothy Stanis
(74) *Attorney, Agent, or Firm* — Kwan & Olynick LLP

(57) ABSTRACT

A trunk supporting exoskeleton comprises: a supporting trunk; thigh links configured to move in unison with a person's thighs; and first and second torque generators located on both left and right halves of the person substantially close to the person's hip. The torque generators couple the supporting trunk to the thigh links, and generate torque between the thigh links and the supporting trunk. When the person bends forward such that a predetermined portion of the supporting trunk passes beyond a predetermined angle from vertical, a torque generator(s) imposes a resisting
(Continued)

torque between the supporting trunk and the thigh link(s), causing the supporting trunk to impose a force against the person's trunk, and the thigh link(s) to impose a force onto the person's thigh. When the predetermined portion does not pass beyond the predetermined angle, the torque generators impose no resisting torques between said supporting trunk and respective thigh links.

27 Claims, 45 Drawing Sheets

Related U.S. Application Data

(60) Provisional application No. 61/495,484, filed on Jun. 10, 2011.

(52) U.S. Cl.
CPC .... *A61H 1/0292* (2013.01); *A61F 2005/0179* (2013.01); *A61H 2201/1246* (2013.01); *A61H 2201/1261* (2013.01); *A61H 2201/164* (2013.01); *A61H 2201/165* (2013.01); *A61H 2201/1619* (2013.01)

(56) References Cited

U.S. PATENT DOCUMENTS

| | | | |
|---|---|---|---|
| 4,256,098 A | 3/1981 | Swan et al. | |
| 4,745,911 A | 5/1988 | Bender | |
| 4,829,989 A | 5/1989 | Deamer et al. | |
| 5,176,622 A | 1/1993 | Anderson et al. | |
| 5,207,635 A | 5/1993 | Richards et al. | |
| 5,259,833 A | 11/1993 | Barnett | |
| 5,275,426 A * | 1/1994 | Tankersley | A61H 3/008 135/67 |
| 5,951,591 A | 9/1999 | Roberts | |
| 6,436,065 B1 | 8/2002 | Mitchell | |
| 7,553,266 B2 | 6/2009 | Abdoli-Eramaki | |
| 7,744,552 B1 | 6/2010 | Babcock | |
| 8,060,945 B2 | 11/2011 | Adarraga | |
| 8,568,344 B2 | 10/2013 | Ferguson et al. | |
| 9,022,956 B2 | 5/2015 | Kazerooni et al. | |
| 2005/0130815 A1 | 6/2005 | Abdoli-Eramaki | |
| 2007/0090143 A1 | 4/2007 | Clayton, III et al. | |
| 2008/0161738 A1 | 7/2008 | Giesen | |
| 2008/0228121 A1 | 9/2008 | Hughes | |
| 2009/0292369 A1 | 11/2009 | Kazerooni et al. | |
| 2010/0094185 A1 * | 4/2010 | Amundson | A61F 5/0102 602/16 |
| 2010/0125230 A1 | 5/2010 | Hurley | |
| 2010/0298746 A1 * | 11/2010 | Shimizu | A61H 3/008 601/35 |
| 2011/0098617 A1 | 4/2011 | Ferguson | |
| 2011/0105966 A1 | 5/2011 | Kazerooni et al. | |
| 2011/0111932 A1 * | 5/2011 | von Hoffmann | A63B 23/0494 482/124 |
| 2011/0266323 A1 | 11/2011 | Kazerooni et al. | |
| 2014/0121573 A1 | 5/2014 | Kazerooni et al. | |

FOREIGN PATENT DOCUMENTS

| | | |
|---|---|---|
| JP | H03165765 A | 7/1991 |
| JP | 2007020672 | 2/2007 |
| JP | 2007097636 | 4/2007 |
| JP | 2007130234 | 5/2007 |
| JP | 2007282991 | 11/2007 |
| JP | 2009011818 | 1/2009 |
| WO | 2010011848 A1 | 1/2010 |

* cited by examiner

TRUNK SUPPORTING EXOSKELETON AND METHOD OF USE

CROSS-REFERENCE TO RELATED APPLICATIONS

This application is a continuation-in-part of U.S. patent application Ser. No. 14/125,117, filed Jun. 11, 2013, which claims priority to PCT application PCT/US12/41891, filed Jun. 11, 2012, which claims the benefit of U.S. patent application 61/495,484, filed Jun. 10, 2011, which are incorporated by reference along with all other references cited in this application.

GOVERNMENT LICENSE RIGHTS

This invention was made with government support under Grant No. 1317978 awarded by the National Science Foundation (NFS). The government has certain rights in the invention.

Activities resulting in the TRUNK SUPPORTING EXOSKELETON AND METHOD OF USE herein were undertaken within the scope of a pre-existing joint development agreement between U.S. Bionics and The Regents of the University of California,

BACKGROUND OF THE INVENTION

The present invention relates generally to exoskeletons, and more particularly, to trunk supporting exoskeletons to reduce muscle forces in a user's back.

In general, back support devices which are configured to assist a person in bending, lifting and/or standing upright are known in the art. U.S. Pat. No. 6,436,065, U.S. Pat. No. 5,951,591, U.S. Pat. No. 5,176,622, and U.S. Pat. No. 7,744,552. U.S. Pat. No. 1,409,326 and U.S. Pat. No. 4,829,989 describe devices where moment is created during a bend to counteract the moments from a person's trunk gravity weight. These systems utilize a passive, spring resistance to create a torque between the wearer's torso and legs. By creating a restorative moment at the hip, the probability of injury of the L5/S1 area of the spine is greatly reduced. Once the angle between torso and leg reaches a predetermined angle during stooping, squatting, or walking, the devices provide resistance; however none of the devices differentiate between walking and bending or sitting and bending. This means the user cannot walk comfortably using these passive devices since the user's legs must push against the devices during walking. Similarly the user cannot sit comfortably using these passive devices since the user's legs must push against the devices during sitting. This is uncomfortable and hazardous, preventing the user from moving around unrestricted, and is the most important reason to avoid the use of these systems in various industrial settings.

BRIEF SUMMARY OF THE INVENTION

The present invention is directed to a trunk supporting exoskeleton which is configured to be worn by a person to reduce the muscle forces in the person's back during forward lumbar flexion. In general the trunk supporting exoskeleton comprises: a supporting trunk which is configured to be coupled to the person's trunk; two thigh links which are configured to move in unison with the person's thighs in a manner resulting in flexion and extension of respective thigh links relative to the supporting trunk; and two torque generators located on both left and right halves of the person substantially close to the person's hip. The torque generators couple the supporting trunk to the respective thigh links and are configured to generate torque between the thigh links and the supporting trunk. In operation when the person bends forward in the sagittal plane such that a predetermined portion of the supporting trunk passes beyond a predetermined angle from the vertical gravity line, at least one of the first or second torque generators imposes a resisting torque between the supporting trunk and at least one of the thigh links. This causes the supporting trunk to impose a force against the person's trunk and at least one of the thigh links to impose a force onto the person's thigh. When the predetermined portion of the supporting trunk does not pass beyond the predetermined angle from the vertical gravity line, the first and second torque generators, during the entire range of motion of the thigh links, impose no resisting torques between the supporting trunk and the respective thigh links.

Other objects, features, and advantages of the present invention will become apparent upon consideration of the following detailed description and the accompanying drawings, in which like reference designations represent like features throughout the FIGS.

BRIEF DESCRIPTION OF THE DRAWINGS

FIG. 42 depicts the coupling device of FIG. 41 in an open position with a strap there through;

FIG. 45 depicts an embodiment of the coupling device of FIG. 44 with a strap there through.

DETAILED DESCRIPTION OF THE INVENTION

Figure 1:
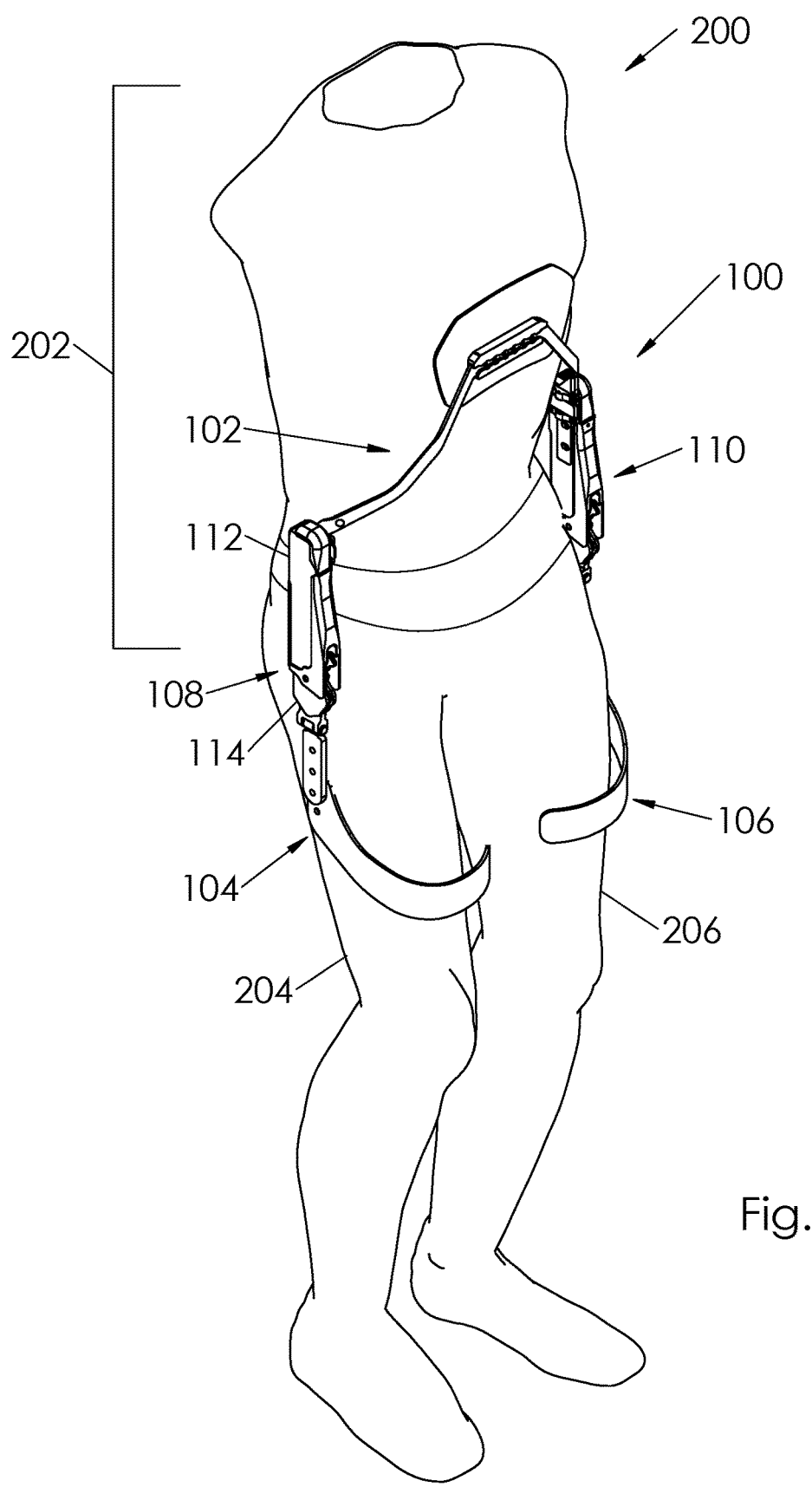
FIG. 1 shows a front perspective view of a user wearing a trunk supporting exoskeleton of the present invention.
Figure 2:
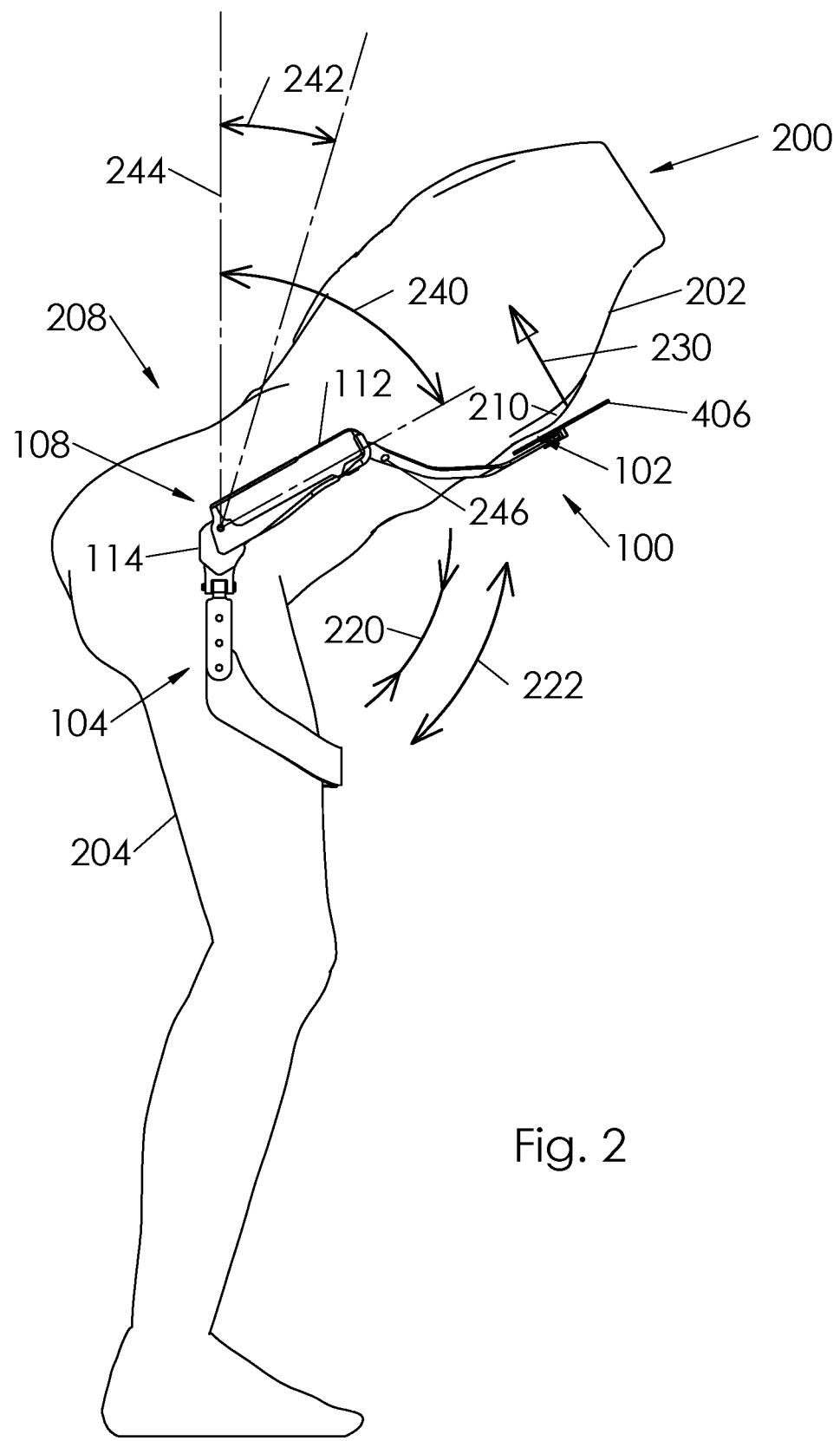
FIG. 2 shows a side view of a trunk supporting exoskeleton of the present invention on a forward leaning person.

FIG. 1 shows an embodiment of Trunk Support Exoskeleton 100. It is configured to be worn by a Person 200 to reduce the muscle forces in the person's back during forward lumbar flexion. FIG. 2 shows person 200 during forward lumbar flexion. Trunk Support Exoskeleton 100 comprises a supporting trunk 102 which is configured to be coupled to person's trunk 202. Person's trunk 202 is defined as the central part of the human from which the neck and limbs extend. The trunk includes the thorax and the abdomen.

Trunk Support Exoskeleton 100 further comprises a first thigh link 104 and a second thigh link 106 which are configured to couple to respective thighs 204 and 206 of person 200. As shown in FIG. 1, first thigh link 104 and second thigh link 106 are configured to move in unison with person's thighs 204 and 206, respectively, in a manner resulting in flexion and extension of respective first and second thigh links 104 and 106 relative to supporting trunk 102. Flexion of first thigh link 104 relative to supporting trunk 102 is defined as when first thigh link 104 and supporting trunk 102 rotate towards to each other. This is shown by arrow 220 in FIG. 2. Flexion of second thigh link 106 relative to supporting trunk 102 is defined similarly. Extension of first thigh link 104 relative to supporting trunk 102 is defined as when first thigh link 104 and supporting trunk 102 rotate away from each other. This is shown by arrow 222 in FIG. 2. Extension of second thigh link 106 relative to supporting trunk 102 is defined similarly.

Trunk support exoskeleton 100 further comprises a first torque generator 108 and a second torque generator 110. First torque generator 108 is configured to generate a torque between first thigh link 104 and supporting trunk 102. Second torque generator 110 is configured to generate a torque between second thigh link 106 and supporting trunk 102. In some embodiments of the invention, first and second torque generators 108 and 110 are located on the left and right halves of person 200 substantially close to person's hip.

In operation, when person 200 bends forward in the sagittal plane such that a predetermined portion of supporting trunk 102 passes beyond a predetermined angle 242 from vertical 244, at least one of the first or second torque generators 108 and 110 imposes a resisting torque between supporting trunk 102 and at least one of the first and second thigh links 104 and 106. This causes supporting trunk 102 to impose a supporting trunk force 230 against person's trunk 202. In the embodiment of FIG. 2, supporting trunk force 230 is generally imposed on person's chest area 210. At the same time, at least one of the first and second thigh links 104 and 106 impose a force onto person's thighs 204 and 206. Supporting trunk force 230 imposed by supporting trunk 102 against person's trunk 202 helps reduce the muscle forces at the person's lower back at the general area of 208.

Figure 3:
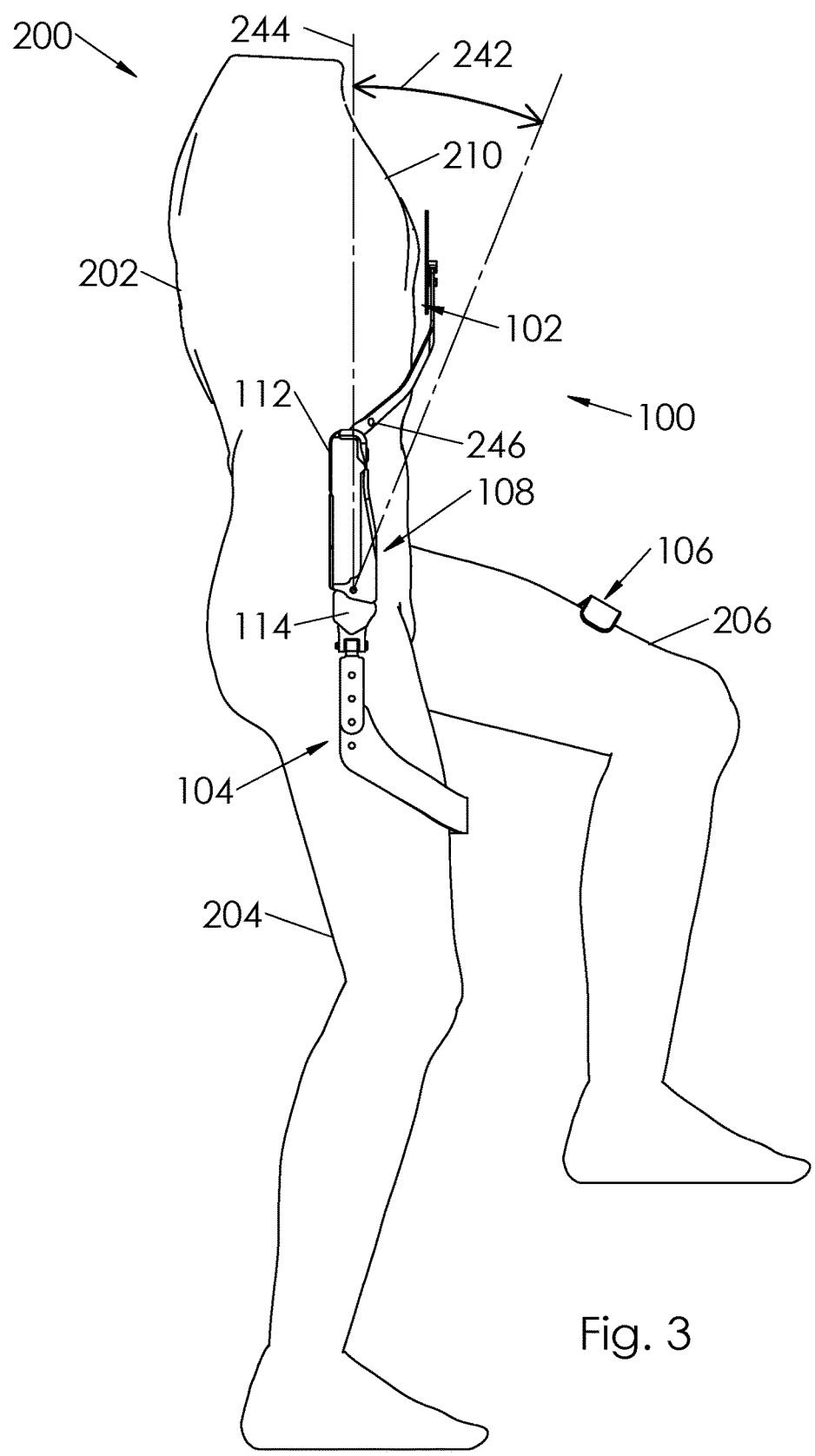
FIG. 3 depicts a side view of a user climbing in a trunk supporting exoskeleton of the present invention.

As shown in FIG. 3, when person 200 is not in a bent position (i.e. when a predetermined portion of supporting trunk 102 does not pass beyond predetermined angle 242 from vertical), first and second torque generators 108 and 110, during the entire range of motion of first and second thigh links 104 and 106, impose no resisting torques between supporting trunk 102 and the respective first and second thigh links 104 and 106. This means as long as person 200 is not in a bent position (i.e. when a predetermined portion of supporting trunk 102 does not pass beyond predetermined angle 242 from vertical 244 as shown in FIG.

3), person 200 can walk, ascend and descend stairs and ramps without any force imposed on person 200 from supporting trunk 102. However, if person 200 bends forward in the sagittal plane (i.e. when a predetermined portion of supporting trunk 102 passes beyond predetermined angle 242 from vertical 244 as shown in FIG. 2), supporting trunk force 230 from supporting trunk 102 will help support person's trunk 202. FIG. 2 shows an example where person 200 is bent. FIG. 3 shows an example where person 200 is not bent. FIG. 2 also shows an embodiment where predetermined angle from vertical is shown by 242. In this embodiment, a predetermined portion of supporting trunk 102 is shown by 246. Since person 200 has bent in FIG. 2 and predetermined portion 246 has passed beyond predetermined angle 242, as represented by arrow 240, supporting trunk force 230 is imposed on person's trunk 202. Examples of predetermined angle 242 can be 5, 10 or 15 degrees. In some embodiments, predetermined angle 242 can be zero. Since person 200 has not bent in FIG. 3, predetermined portion 246 has not passed beyond predetermined angle 242 and no force is imposed on person's trunk 202.

Figure 4:
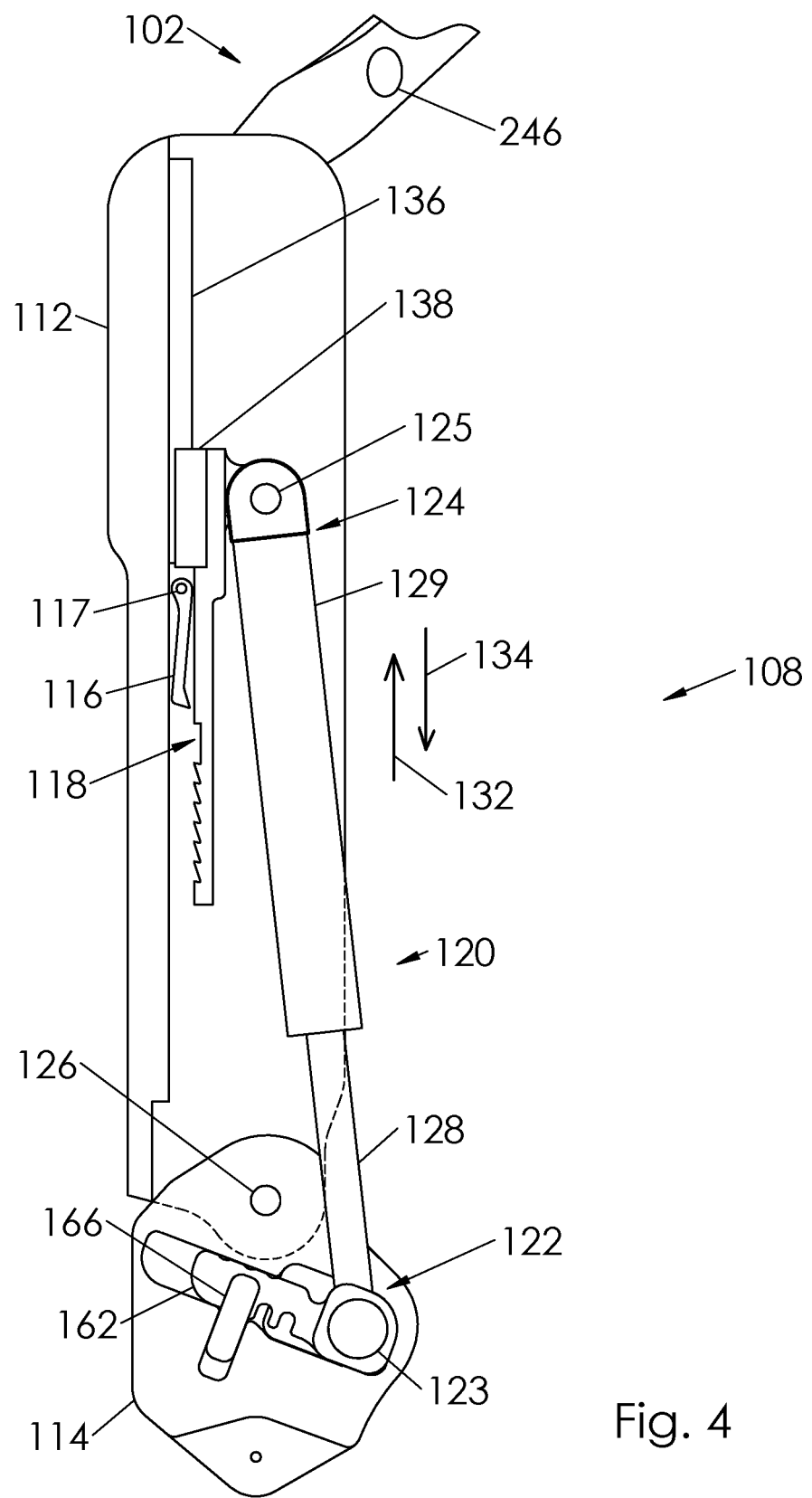
FIG. 4 depicts an embodiment of the torque generator in an upright position.

FIG. 4 shows an embodiment of first torque generator 108. Second torque generator 110 is a mirrored body of first torque generator 108 thus only first torque generator 108 is described here. In embodiments, first torque generator 108, in addition to other components, comprises an upper bracket 112 configured to be coupled to supporting trunk 102. Supporting trunk 102 is not shown in FIG. 4, but this coupling is shown in FIGS. 1 and 2. First torque generator 108 further comprises a lower bracket 114 which is configured to be coupled to first thigh link 104, and rotatably coupled to upper bracket 112 around exoskeleton joint 126. In some embodiments of the invention, upper bracket 112 and lower bracket 114 rotate relative to each other round exoskeleton joint 126. First torque generator 108 further comprises pendulum 116 which is rotatably coupled to upper bracket 112 around pendulum joint 117. First torque generator 108 also comprises an engagement bracket 118 which is slidingly coupled to upper bracket 112. Arrows 132 and 134 show the sliding motion between engagement bracket 118 and upper bracket 112. In the embodiment of FIG. 4, the sliding motion is provided by rail 136 and carriage 138. Rail 136 is mounted on upper bracket 112. Carriage 138 is mounted on engagement bracket 118. First torque generator 108 additionally comprises a compression spring 120 which is rotatably coupled to lower bracket 114 from its first end 122 around first end joint 123. Compression spring 120 is also rotatably coupled to engagement bracket 118 from its second end 124 around second end joint 125. In some embodiments of the invention as shown in FIG. 4, compression spring 120 is a gas spring comprised of a rod 128 and a cylinder 129. In embodiments, first torque generator 108 also includes locking pin 166 is used to lock the position of sliding block 162 in channel 160.

In operation, when a predetermined portion 246 of supporting trunk 102 passes beyond predetermined angle 242 (as shown FIG. 5), pendulum 116 comes into contact with engagement bracket 118. This prevents engagement bracket 118 from sliding, causing compression spring 120 to be able to provide a resisting torque between upper bracket 112 and lower bracket 114. Further, when a predetermined portion of supporting trunk 102 does not pass beyond predetermined angle 242 (as shown in FIG. 6), pendulum 116 is not in contact with engagement bracket 118. This causes engagement bracket 118 to be free to slide on upper bracket 112. This means in this configuration, compression spring 120 is uncompressed and does not provide resisting torque between upper bracket 112 and lower bracket 114. In this situation, person 200 can walk, ascend and descend stairs and ramps freely.

Figure 5:
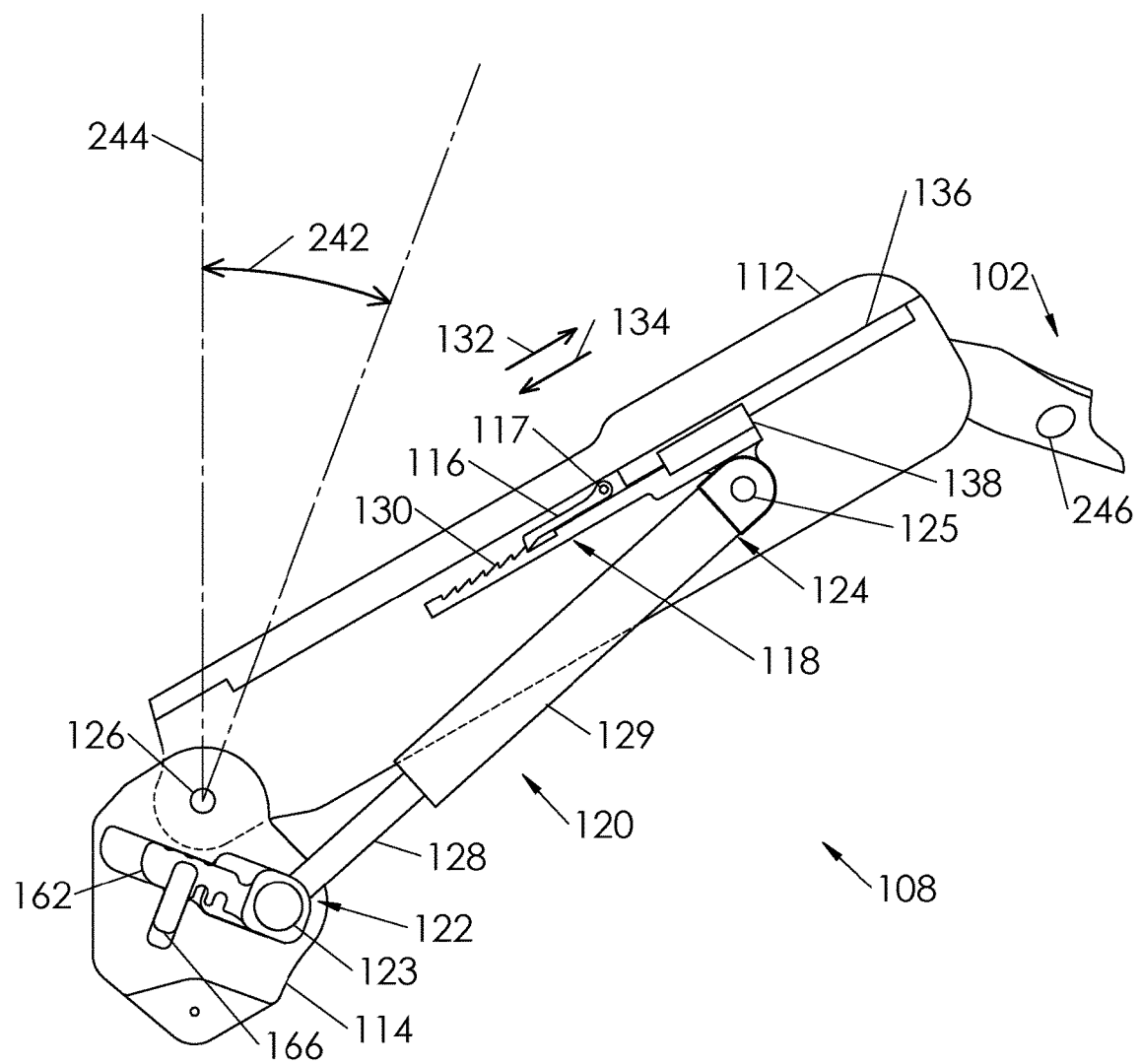
FIG. 5 depicts an embodiment of the torque generator in an angled position.
Figure 6:
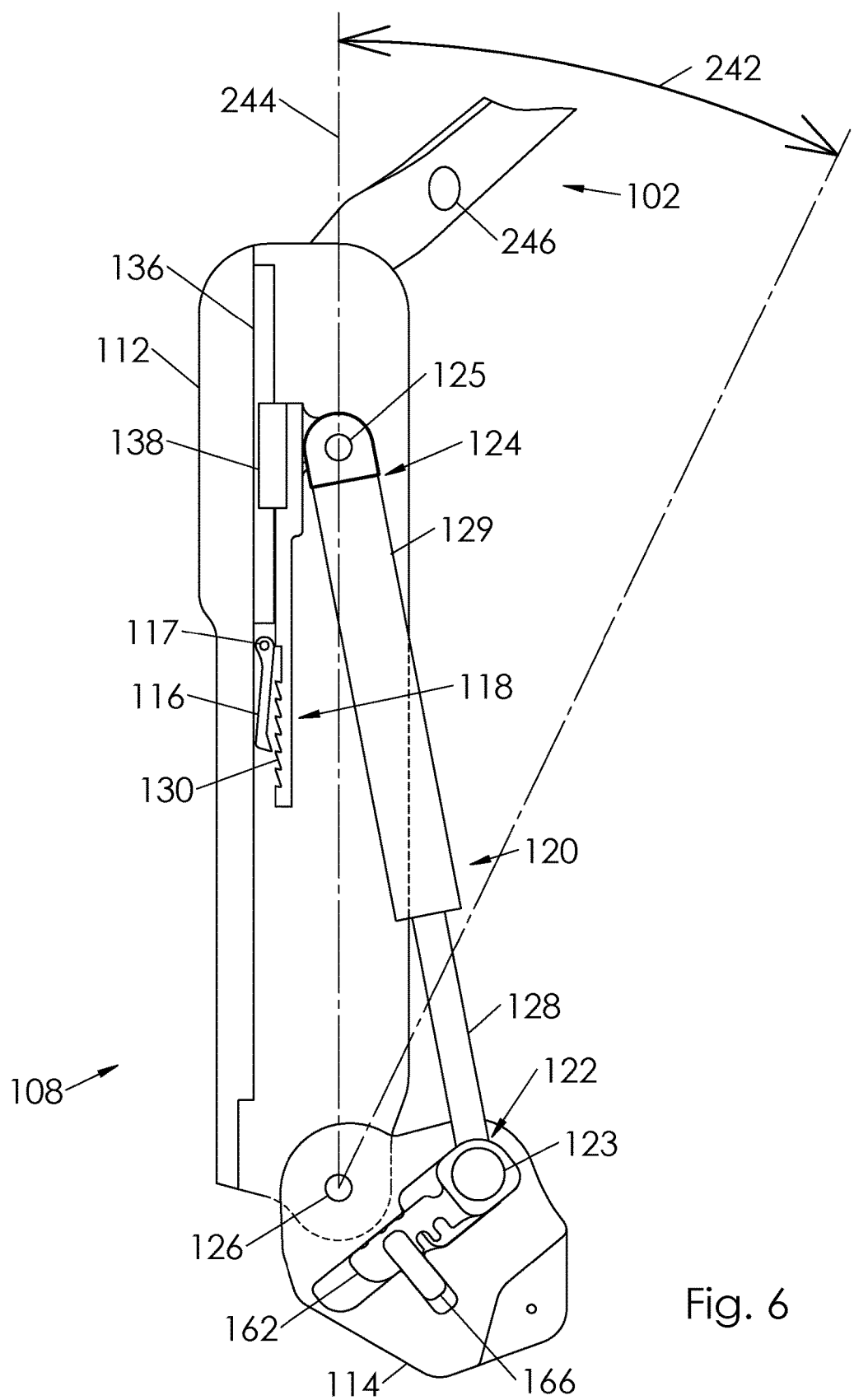
FIG. 6 depicts an embodiment of the torque generator with respect to a predetermined position.

FIGS. 5 and 6 show an embodiment of engagement bracket 118. In this embodiment, engagement bracket 118 comprises a few teeth 130. Engagement bracket 118 and pendulum 116 form a ratchet mechanism. A ratchet mechanism is a mechanical device that allows continuous linear or rotary motion in only one direction while preventing motion in the opposite direction. When pendulum 116 is in contact with engagement bracket 118, engagement bracket 118 cannot slide relative to pendulum 116 and upper bracket 112 along first direction 132, but is free to move along second direction 134. FIG. 5 shows a situation where a predetermined portion of supporting trunk 102 has passed beyond predetermined angle 242. Pendulum 116 has come into contact with engagement bracket 118 due to its weight force (i.e. under the force of gravity the weight of pendulum 116 causes it to swing into contact with engagement bracket 118). This prevents engagement bracket 118 from sliding along direction 132. This causes compression spring 120 to be compressed and to provide a resisting torque between upper bracket 112 and lower bracket 114.

Figure 7:
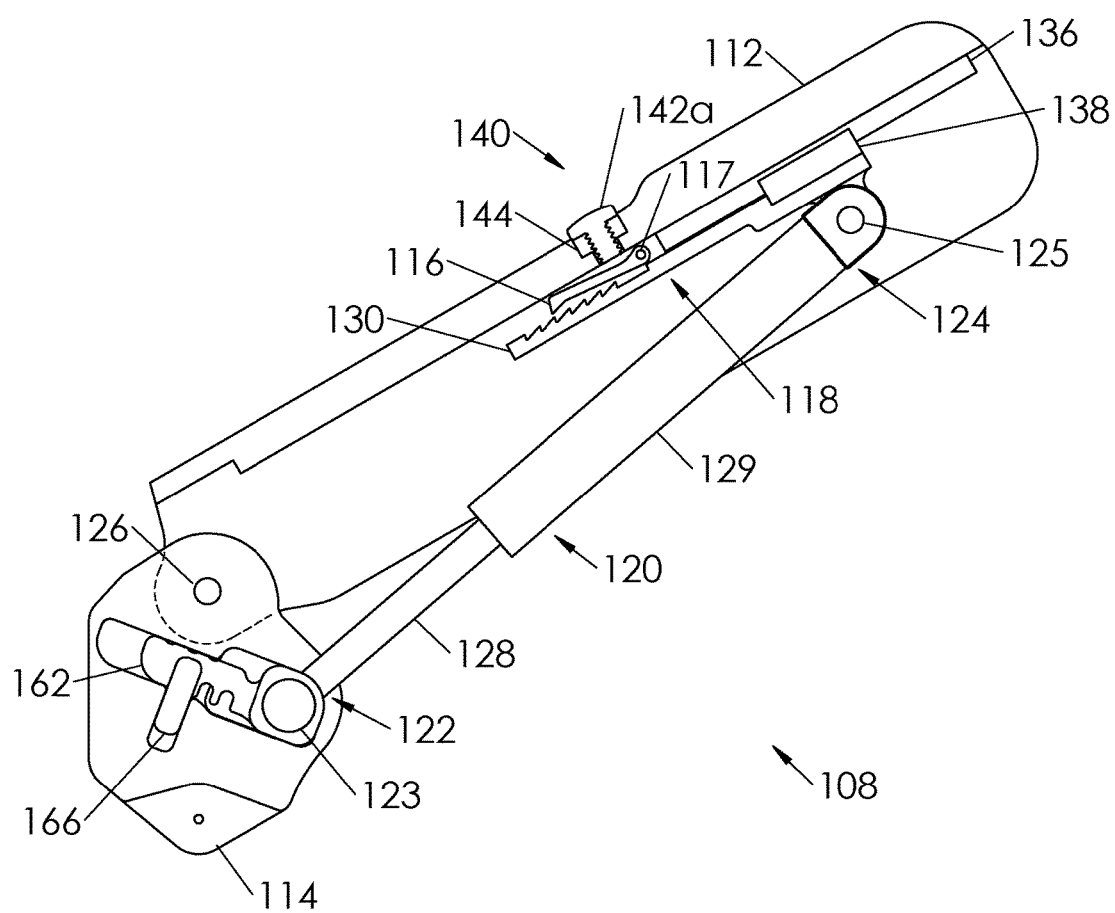
FIG. 7 depicts an embodiment of the torque generator with an angle adjustment mechanism.
Figure 8:
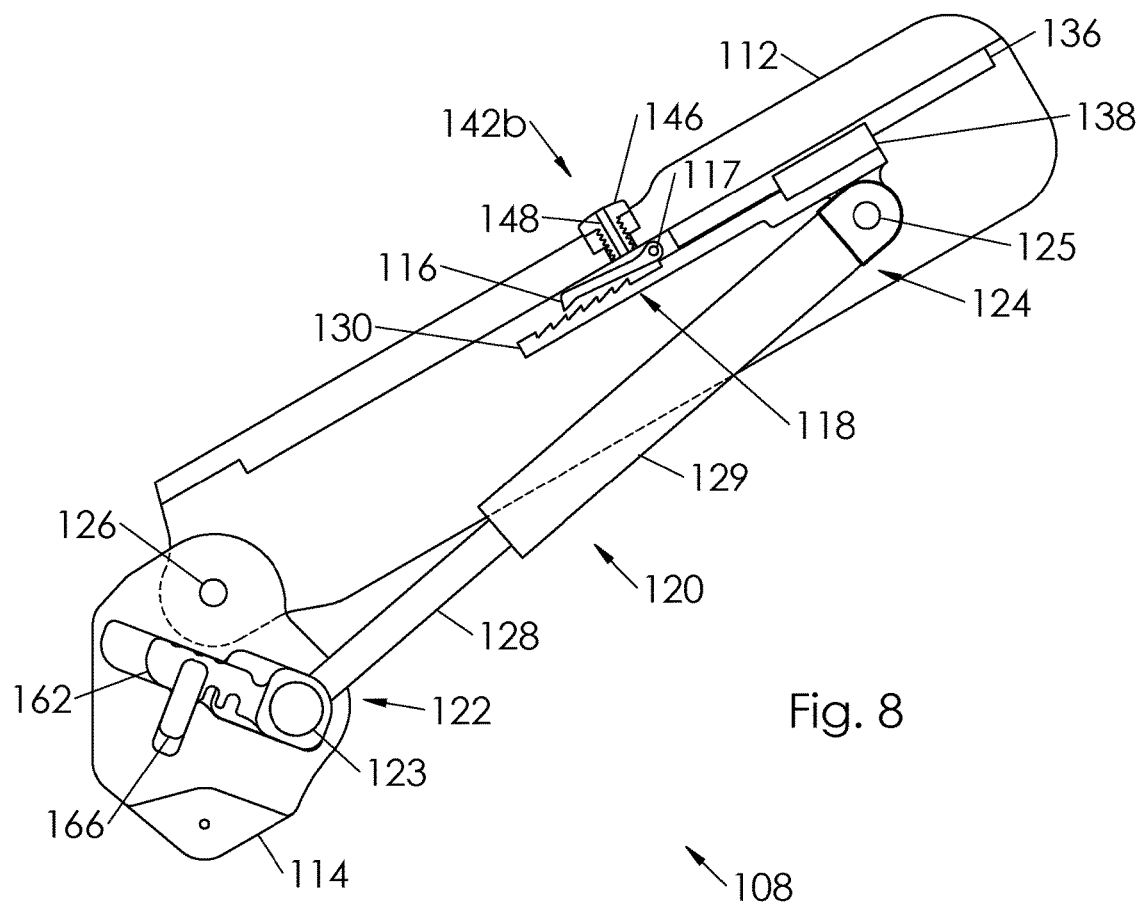
FIG. 8 depicts an embodiment of the torque generator with a magnetic adjustment screw.

FIG. 7 shows an embodiment of first torque generator 108. In this embodiment, first torque generator 108 further comprises of an angle adjustment mechanism 140 that allows the adjustment of predetermined angle 242. Adjustment mechanism 140 can be used to modify predetermined angle 242. In some embodiments as shown in FIG. 7 pendulum 116 is magnetic. Angle adjustment mechanism 140 further comprise a magnetic adjustment screw 142a located in an adjustment screw hole 144 on upper bracket 112 in close proximity to pendulum 116. In operation, when magnetic adjustment screw 142a is turned to change its position relative to pendulum 116, predetermined angle 242 changes. The closer magnetic adjustment screw 142a is to pendulum 116, the larger predetermined angle 242 would be. This is true because when magnetic adjustment screw 142a gets closer to pendulum 116, supporting trunk 102 and consequently upper bracket 112 have to bend more in order for the gravity force acting on pendulum 116 to overcome the magnetic force attracting pendulum 116 to magnetic adjustment screw 142a. Adjustment mechanism 140 can be used to set predetermined angle 242 at desired angle. FIG. 8 shows an embodiment of magnetic adjustment screw 142b. In this embodiment, magnetic adjustment screw 142b is comprised of an adjustment fastener 146 and an adjustment magnet 148 where adjustment magnet 148 is coupled to adjustment fastener 146. In some embodiments of invention, as shown in FIG. 8, adjustment magnet 148 is inserted into adjustment fastener 146.

Figure 9:
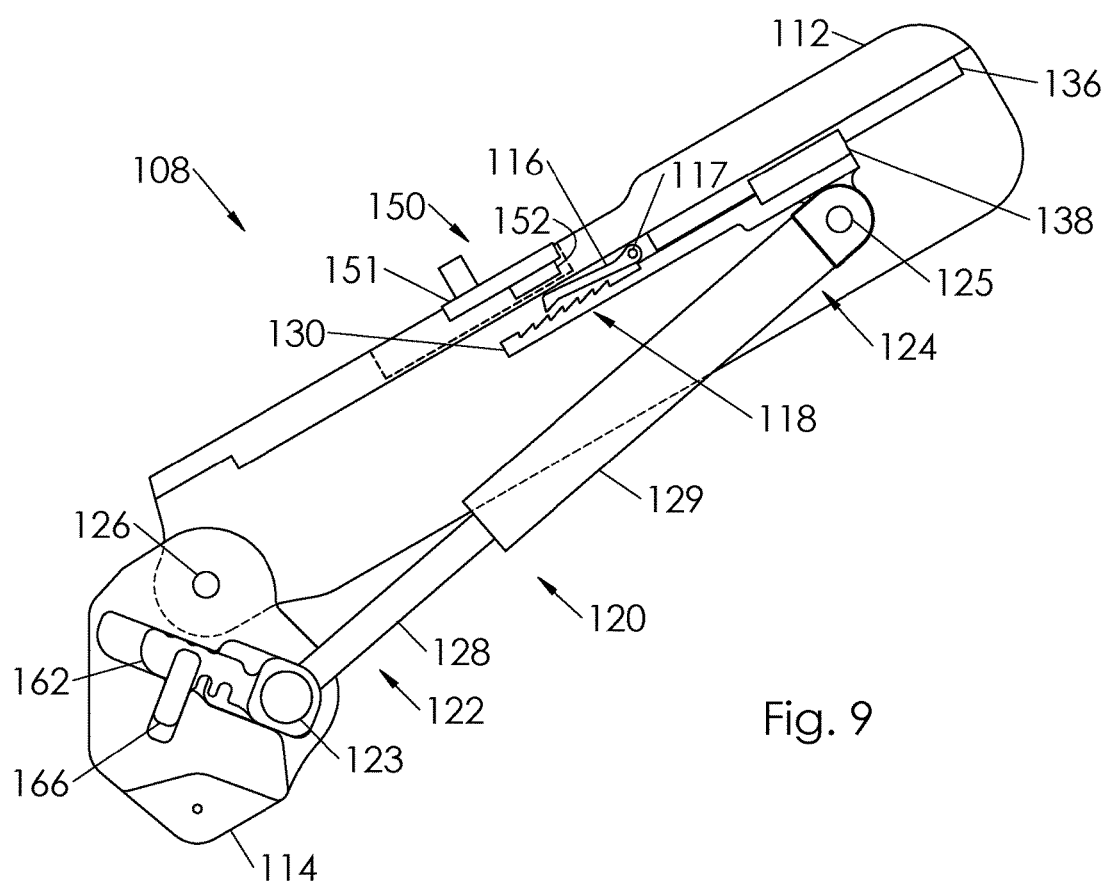
FIG. 9 depicts an embodiment of the torque generator including a manual override mechanism in a first position.
Figure 10:
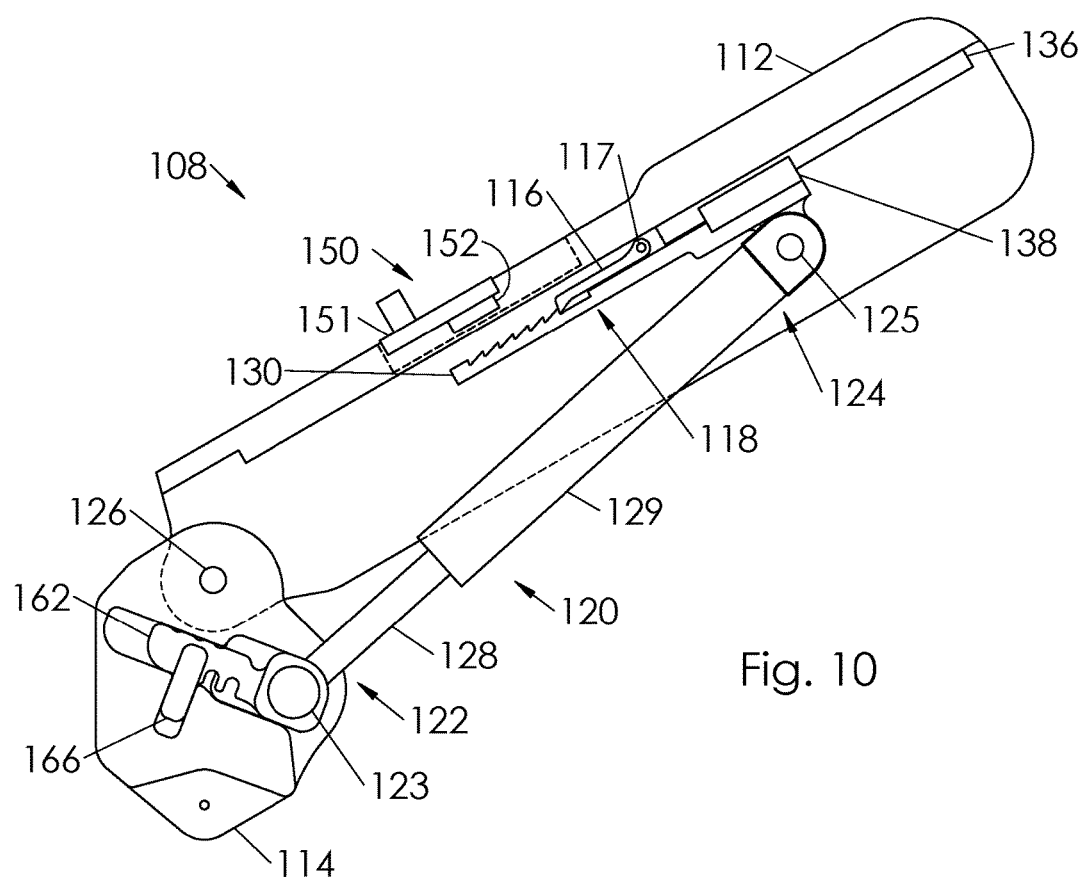
FIG. 10 depicts an embodiment of the torque generator including a manual override mechanism in a second position.

FIG. 9 shows an embodiment of torque generator 108 where a manually manipulated override mechanism 150 is used to completely prevent pendulum 116 from contacting engagement bracket 118, and hence deactivate torque generator 108. In some embodiments of invention, as shown in FIG. 9, pendulum 116 is magnetic and override mechanism 150 comprises of an override slider 151 sliding on upper bracket 112, and an override magnet 152 coupled to override slider 151. In operation, when a user shifts override slider 151 to its override position as shown in FIG. 9, override magnet 152 attracts pendulum 116 to its non-contacting position allowing engagement bracket 118 to move freely. When override slider 151 is moved to its non-override position as shown in FIG. 10, override magnet 152 does not attract pendulum 116 to its non-contacting position, allowing pendulum 116 to come into contact with engagement bracket 118 when a predetermined portion of supporting trunk 102 passes beyond predetermined angle 242. An ordinary person in the art would understand that there can be other methods of preventing pendulum 116 from contacting engagement bracket 118.

Figure 11:
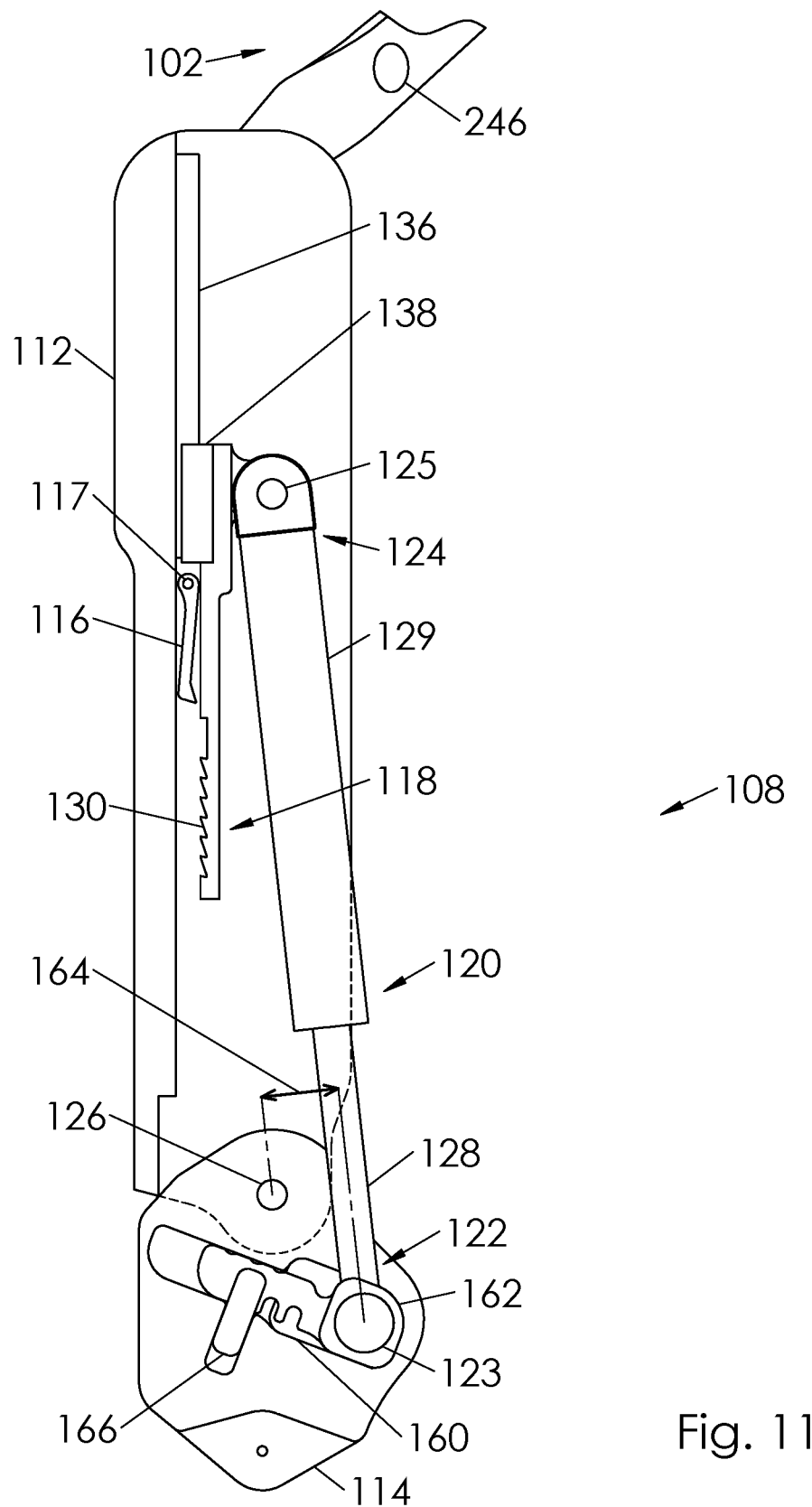
FIG. 11 depicts an embodiment of the torque generator with a compression spring in a first position.
Figure 12:
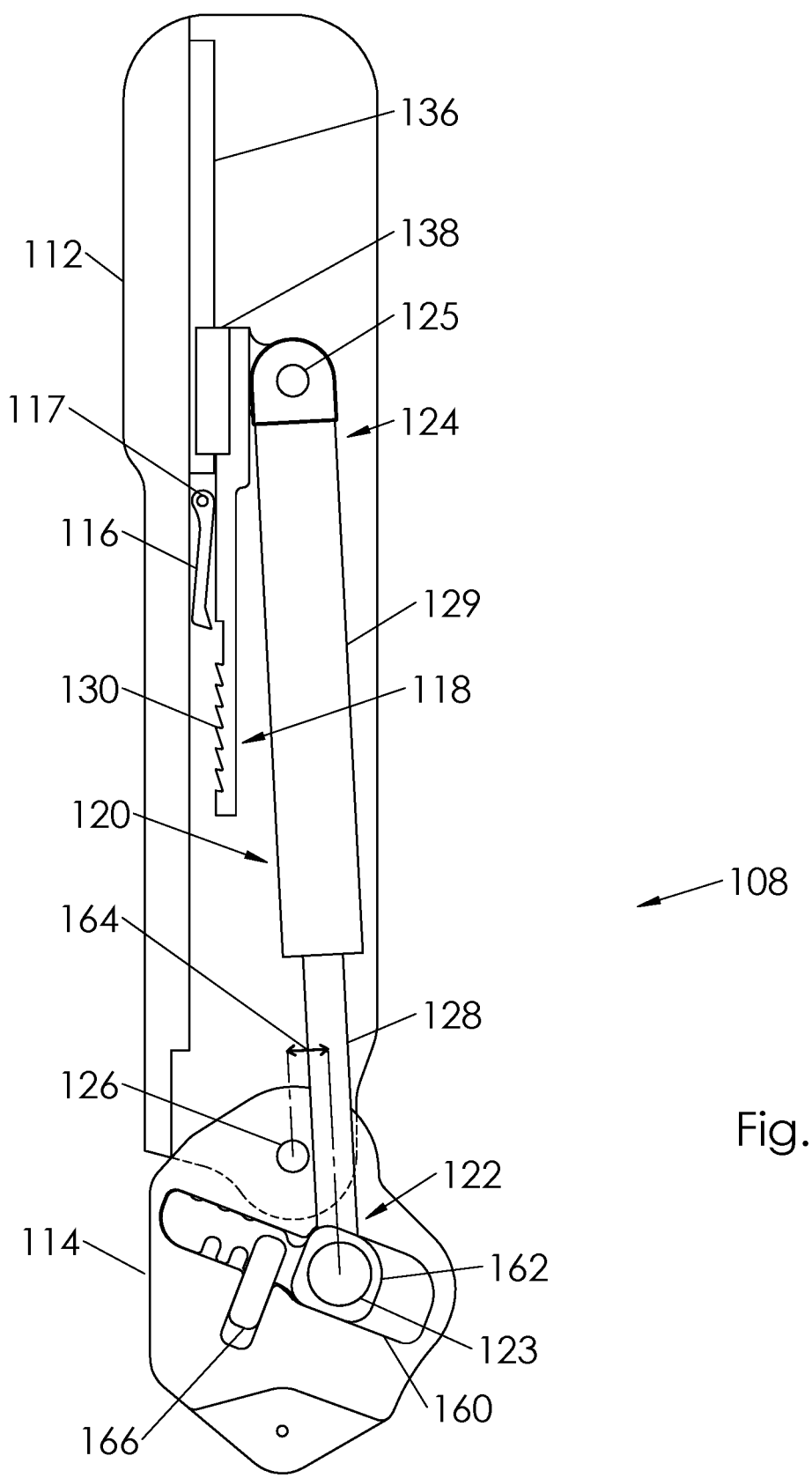
FIG. 12 depicts an embodiment of the torque generator with a compression spring in a second position.

The location of compression spring 120 relative to exoskeleton joint 126 determines the magnitude of torque output of torque generator 108. One can change the location of first end 122 of compression spring 120 to produce various torques. FIG. 11 shows a situation where the location of first end 122 of compression spring 120 is at a distance 164 from exoskeleton joint 126 which is farther than the distance 164 in FIG. 12, allowing for more torque. Accordingly, FIG. 12 shows the situation where the first end 122 of compression spring 120 is located closer to exoskeleton joint 126, wherein it produces less torque. A comparison of spring distance 164 in FIGS. 11 and 12 show more torque can be provided when spring distance 164 is larger. In some embodiments of invention, this torque adjustment is accomplished by changing the position of sliding block 162 inside a channel 160. Sliding block 162 is rotatably coupled to first end 122 of compression spring 120 and is capable of having several positions in channel 160. Channel 160 is formed inside lower bracket 114. In operation, adjusting the position of sliding block 162 in channel 160 allows for various positions of compression spring 120 relative to exoskeleton joint 126 thus various torque levels. Locking pin 166 is used to lock the position of sliding block 162 in channel 160. As can be seen in FIGS. 11 and 12 sliding block 162 has three positions. These positions are determined by three notches in sliding block 162. By positioning sliding block 162 in various locations and locking it by locking pin 166, one can provide various level of torque.

Figure 13:
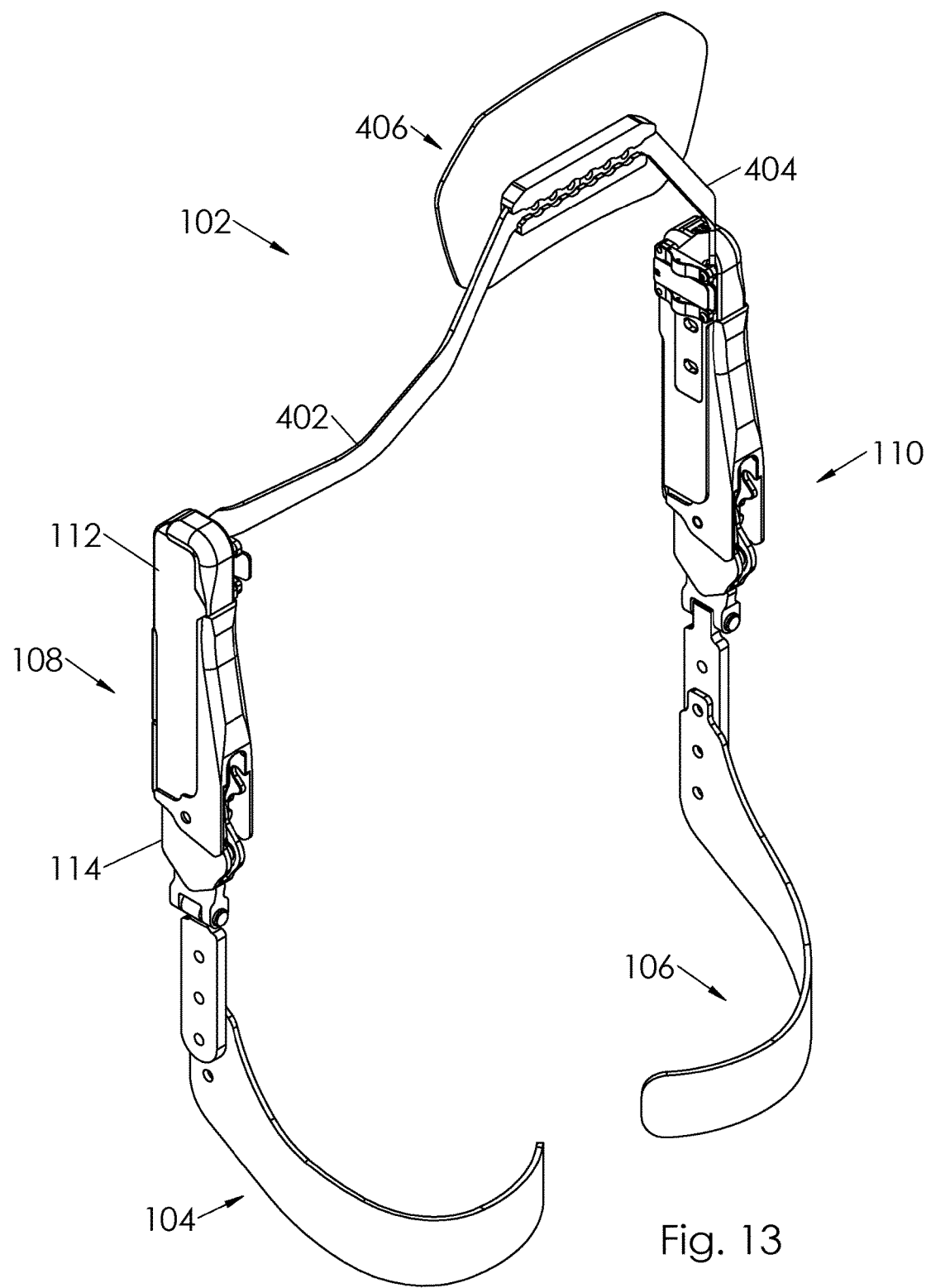
FIG. 13 is an enlarged front perspective view of a supporting trunk of the present invention.
Figure 14:
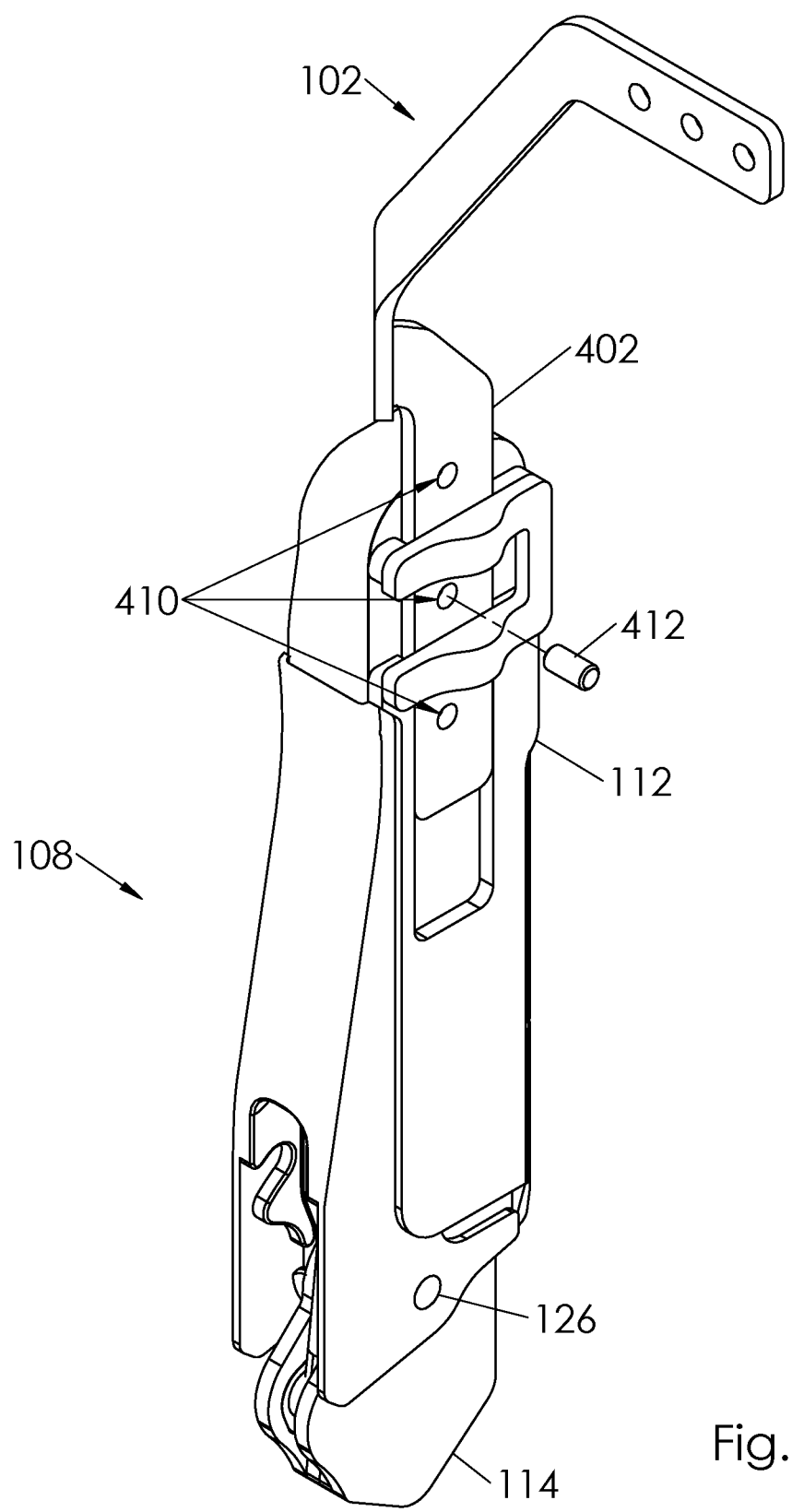
FIG. 14 is a back perspective view of an embodiment of the torque generator of the present invention including side brackets.
Figure 15:
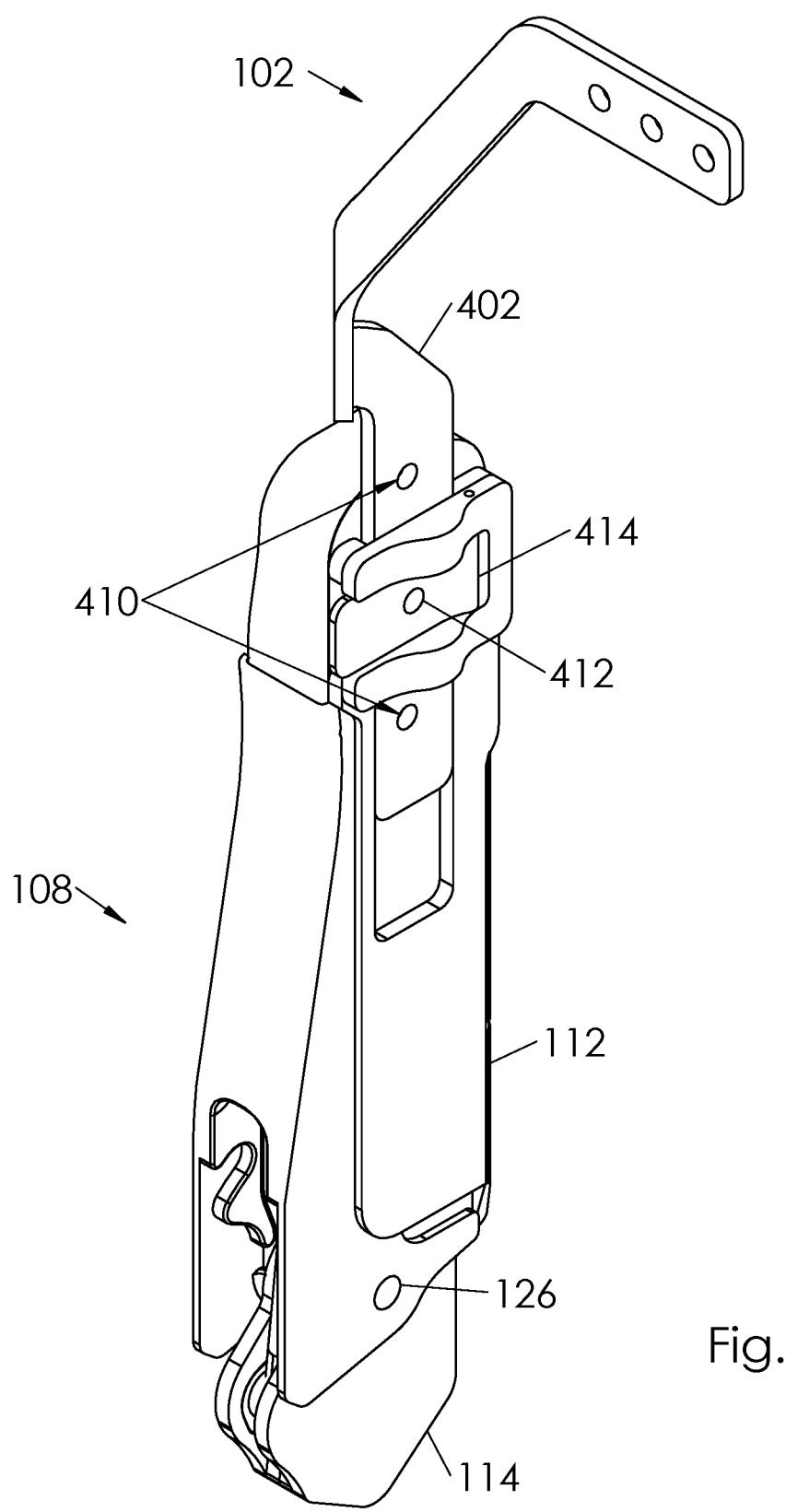
FIG. 15 is a back perspective view an embodiment of the supporting trunk of the present invention including side brackets in a locked position.
Figure 16:
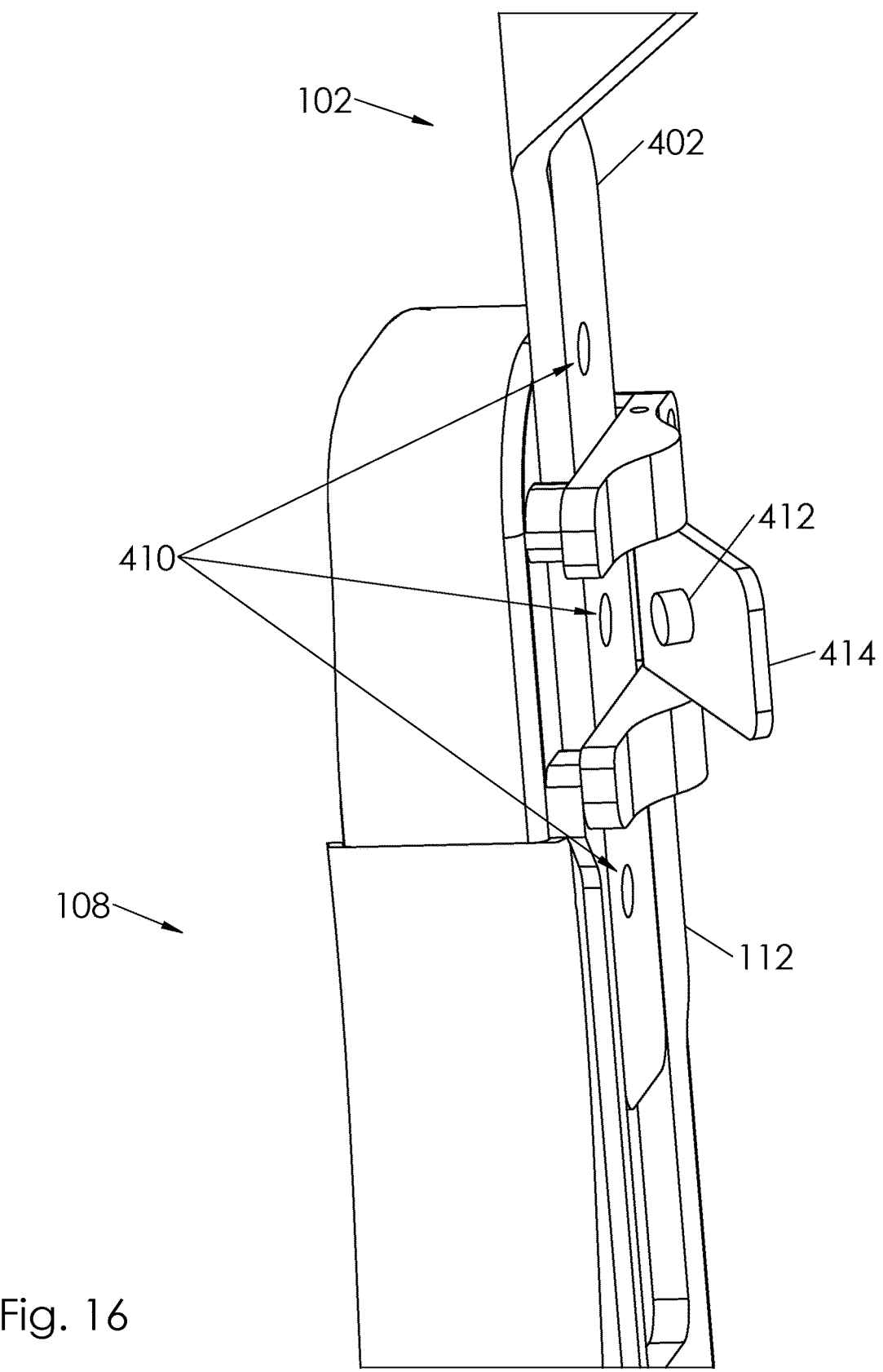
FIG. 16 is an enlarged side perspective view of an adjustment of supporting trunk of the present invention.

FIG. 13 shows an embodiment of supporting trunk 102. In this embodiment, supporting trunk 102 comprises first and second side brackets 402 and 404 which are coupled to first and second torque generators 108 and 110. Supporting trunk 102 further comprises a chest plate 406 which is in contact with person 200. In particular, chest plate 406 is in contact with the front of person's trunk 202 in the general area of said person's chest 210 to impose supporting trunk force 230, as depicted in FIG. 2. In operation, when person 200 bends forwardly and torque generators 108 and 110 are engaged, chest plate 406 of supporting trunk 102 imposes supporting trunk force 230 against the person's trunk 202 and onto the person's chest area. As shown in the embodiment of FIG. 13, the location of two side brackets 402 and 404 can be adjusted relative to first and second torque generators 108 and 110 to hold chest plate 406 in proper position. FIG. 13 shows an embodiment of the invention where the position of side brackets 402 and 404 can be adjusted. As can be seen in FIG. 14, side bracket 402 comprises several side bracket holes 410, and torque generator 108 comprises at least one pin 412. The choice of one of the side bracket holes 410 which at least one pin 412 can be inserted assigns the location of side bracket 402 relative to torque generator 108. FIGS. 15 and 16 show in some embodiments, pin 412 is coupled to torque generator 108 through a spring loaded plate 414. Spring loaded plate 414 has two positions. In operation, when spring loaded plate 414 is in its first position, pin 412 will pass through one of the side bracket holes 410 and side bracket 402 is not free to slide. When spring loaded plate 414 is in its second position as shown in FIG. 16, pin 412 is not inserted in any side bracket hole 410 and side bracket 402 is free to slide in torque generator 108.

Figure 17:
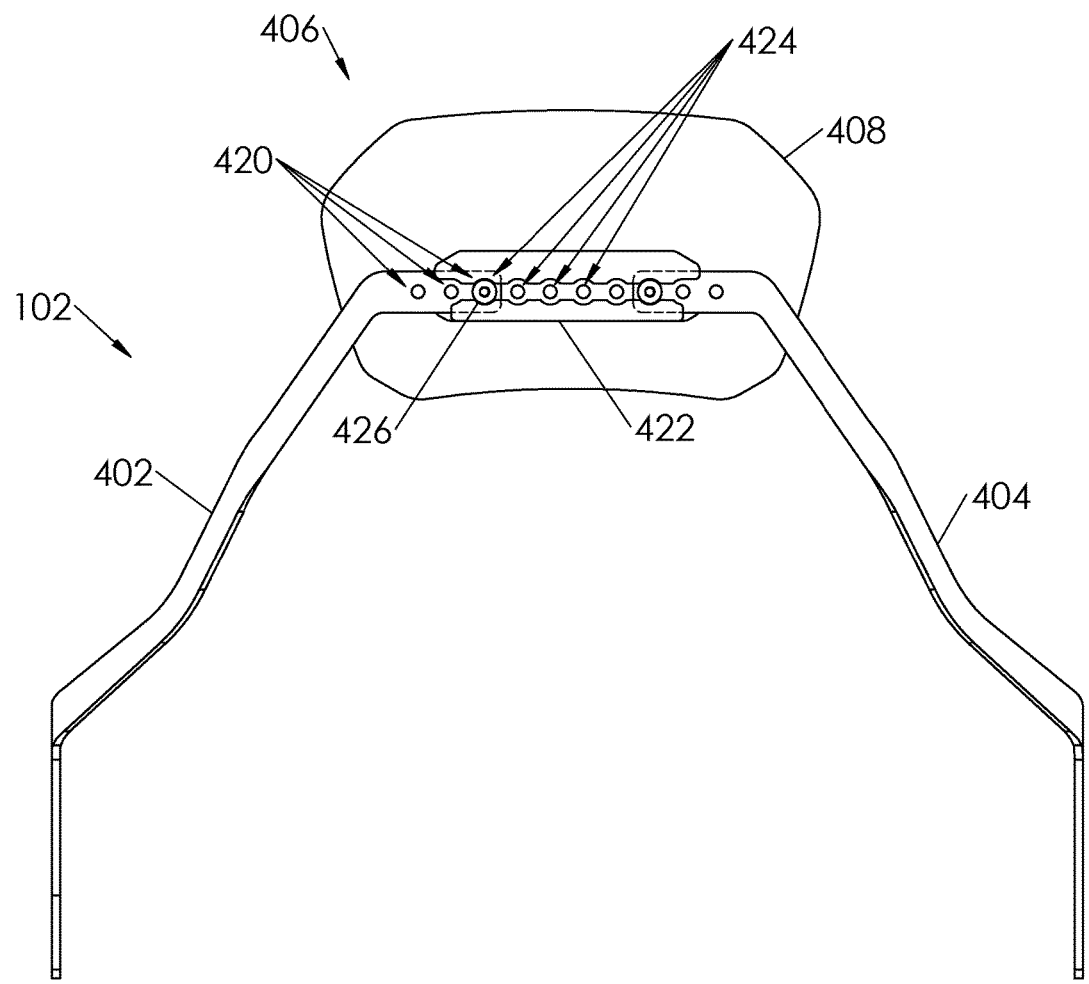
FIG. 17 is a back view of a chest plate and side brackets of the present invention.

FIG. 17 shows an embodiment of the invention wherein the horizontal distance between side brackets 402 and 404 can be adjusted through adjusting the coupling locations of side brackets 402 and 404 relative to chest plate 406. In this embodiment, side bracket 402 comprises width adjustment holes 420. Chest plate 406 comprises a chest channel 422. Chest channel 422 comprises several chest plate holes 424. The connection of chest plate 406 to side bracket 402 with the help of fasteners 426 passing through width adjustment holes 420 and chest plate holes 424 results in adjustment of the width of supporting trunk 102. FIG. 17 shows an embodiment where chest plate 406 further comprises a chest pad 408. Chest pad 408 is capable of moving and rotating relative to said chest channel 422. In some embodiments, the motion and rotation of chest pad 408 relative to chest channel 422 are limited in magnitude. These rotations allow for minor movement of person 200 relative to chest plate 406. During operation, when person 200 bends supporting trunk force 230 is applied by chest plate 406 onto person's chest 210, as depicted in FIG. 2. It is important that supporting trunk force 230 is distributed on an area where the force distribution remains rather normal to the person chest. To this end, chest pad 408 has all the possible degrees of freedom relative to chest channel 422. These degrees of freedom ensure force distributions remain rather normal to the person's chest contour. Additionally, no rubbing forces will take place between person's chest 210 and chest pad 408.

Figure 21:
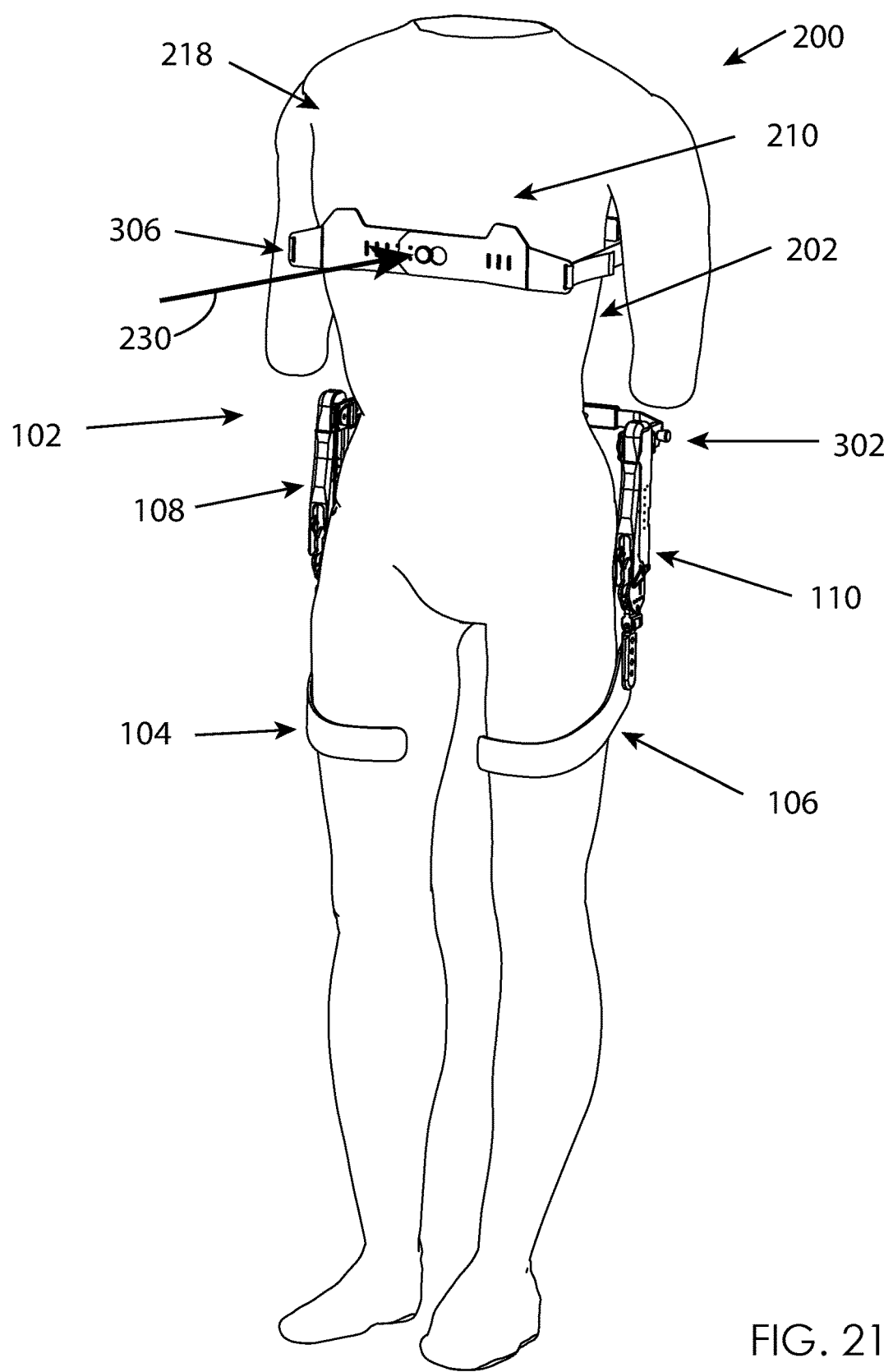
FIG. 21 depicts an anterior three-quarters view showing an embodiment of the trunk supporting exoskeleton worn by a person.
Figure 22:
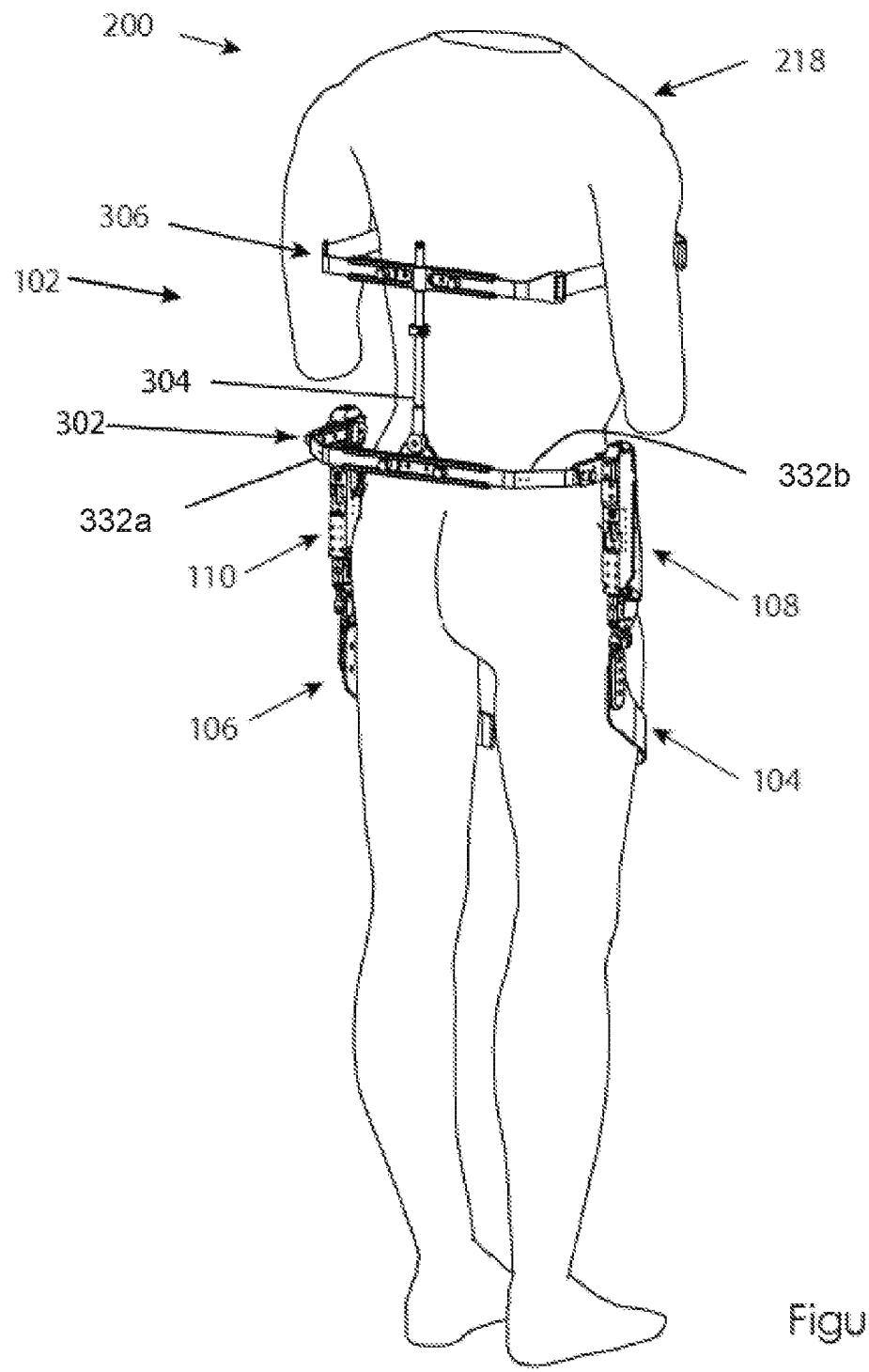
FIG. 22 depicts a posterior three-quarters view showing the trunk supporting exoskeleton in FIG. 21 worn by a person.
Figure 23:
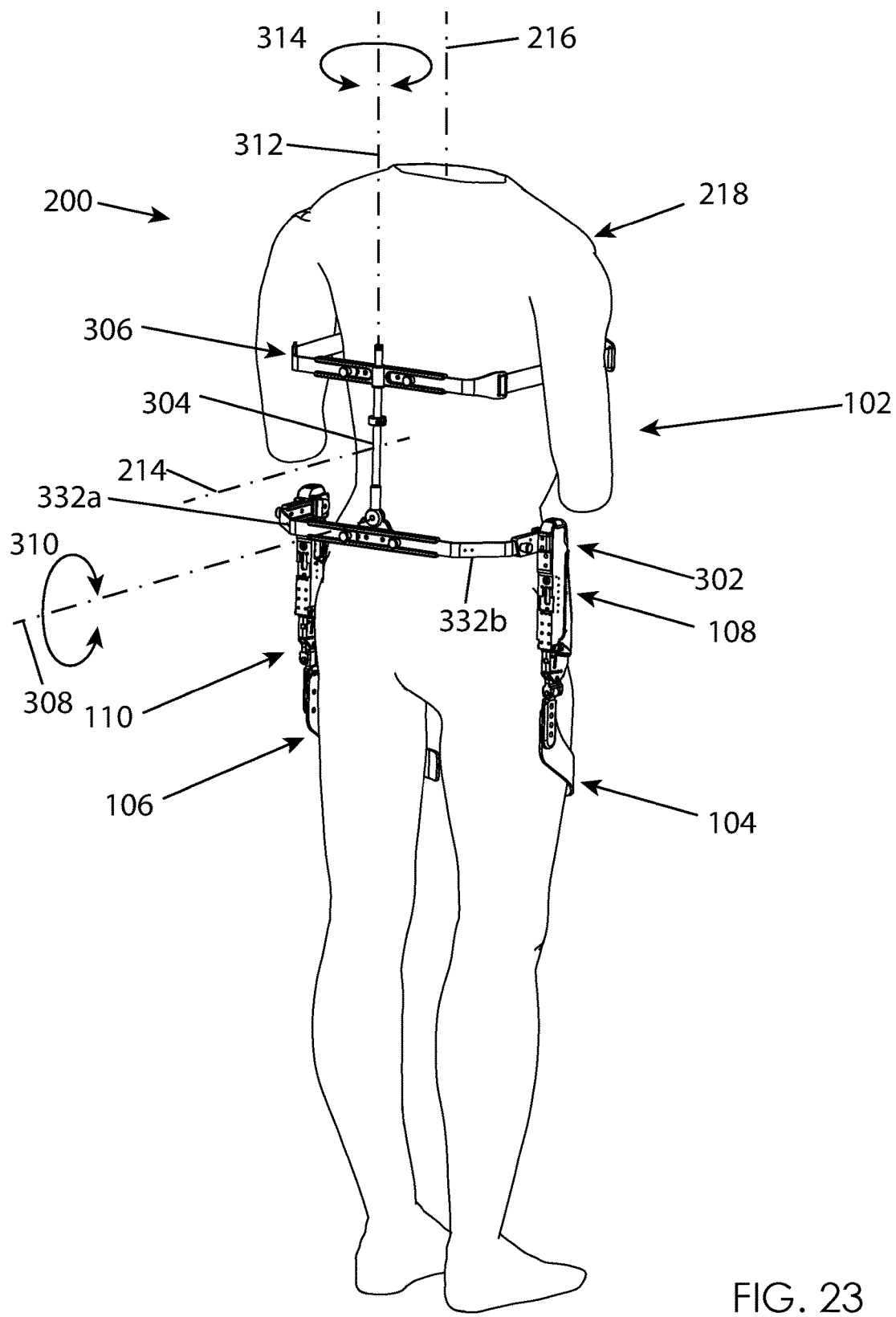
FIG. 23 depicts a posterior three-quarters view showing an embodiment of the trunk supporting exoskeleton with spine rotation capabilities being worn by a person.

FIGS. 21 and 22 show two views of another embodiment of supporting trunk 102 worn by person 200. Supporting trunk 102 comprises a lower frame 302 which is substantially located behind person 200. Lower frame 302 is configured to partially surround person's trunk 202 and is coupled to first and second torque generators 108 and 110 from two sides of person 200. Supporting trunk 102 further comprises a spine frame 304 which is located behind person 200, as depicted in FIG. 22. Spine frame 304, in some embodiments of the invention, is rotatably coupled to lower frame 302. Supporting trunk 102 additionally comprises an upper frame 306 which is coupled to spine frame 304. In some embodiments of the invention, upper frame 306 is configured to be in contact with the general area of person's trunk 202 to impose force 230 on front part of person's trunk 202. In some embodiments of the invention, upper frame 306 is in contact with the general chest area 210 of person's trunk 202 to impose force 230. In some embodiments of the invention, upper frame 306 is in contact with the general shoulder area 218 of person's trunk 202 to impose force 230. Spine frame 304 in some embodiments rotates relative to lower frame 302 along an axis substantially parallel to one of the person's lumbar spine mediolateral flexion and extension axes 214. As shown in FIG. 23, spine frame 304 rotates about axis 308 with respect to lower frame 302. Axis 308 is substantially parallel to one of the person's lumbar spine mediolateral flexion and extension axes 214. Arrow 310 shows the direction of rotation of spine frame 304 relative to lower frame 302 about axis 308. In some embodiments, spine frame 304 rotates relative to lower frame 302 along an axis 312 substantially parallel to person's cranial-caudal axis 216. Arrow 314 shows the direction of this rotation about axis 312.

Figure 24:
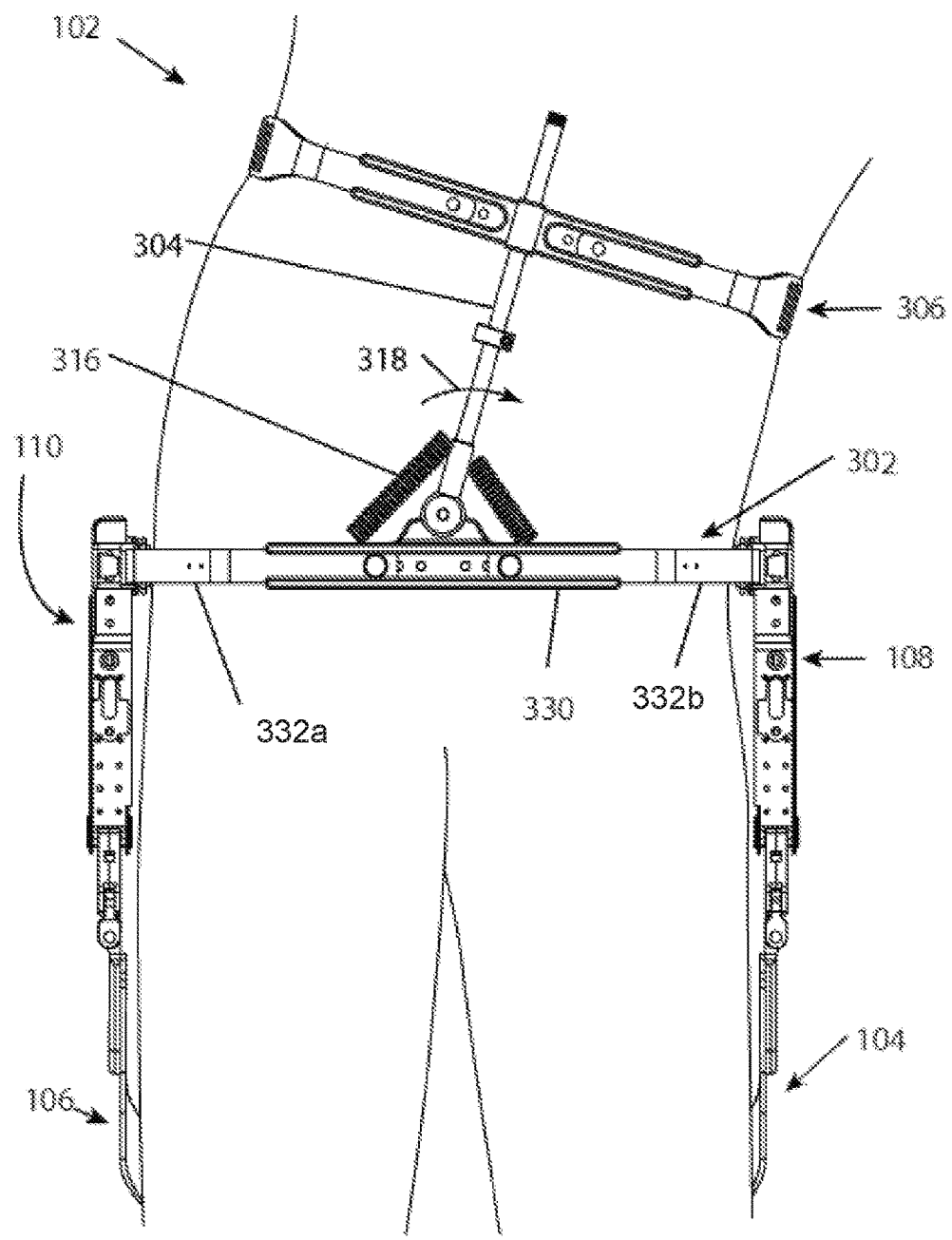
FIG. 24 depicts a posterior view showing the trunk supporting exoskeleton of FIG. 23 worn by a person with resistive elements to resist lateral spine rotation.
Figure 25:
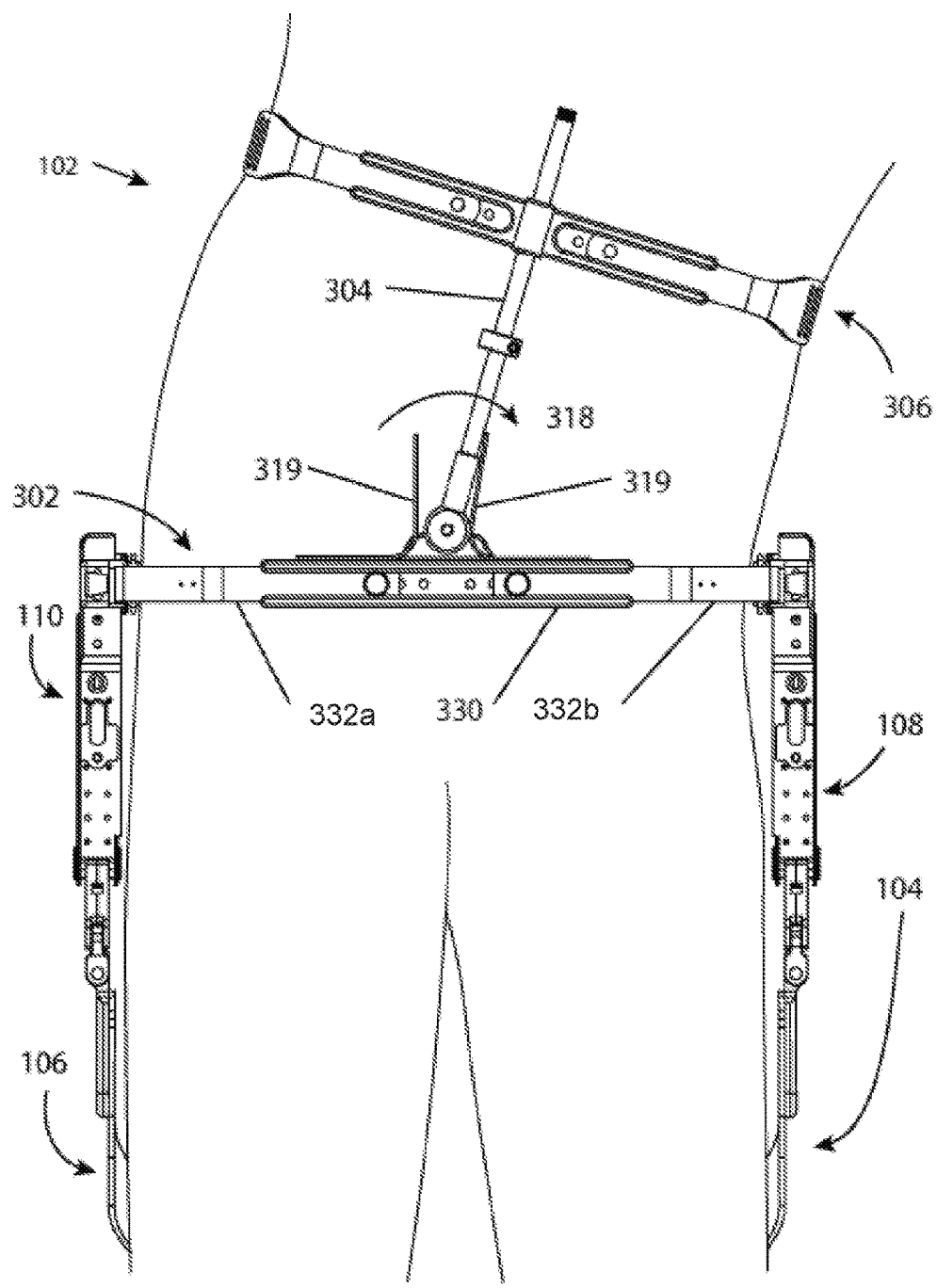
FIG. 25 depicts a posterior view showing the embodiment of FIG. 24 being worn by a person wherein the resistive elements are leaf springs.
Figure 26:
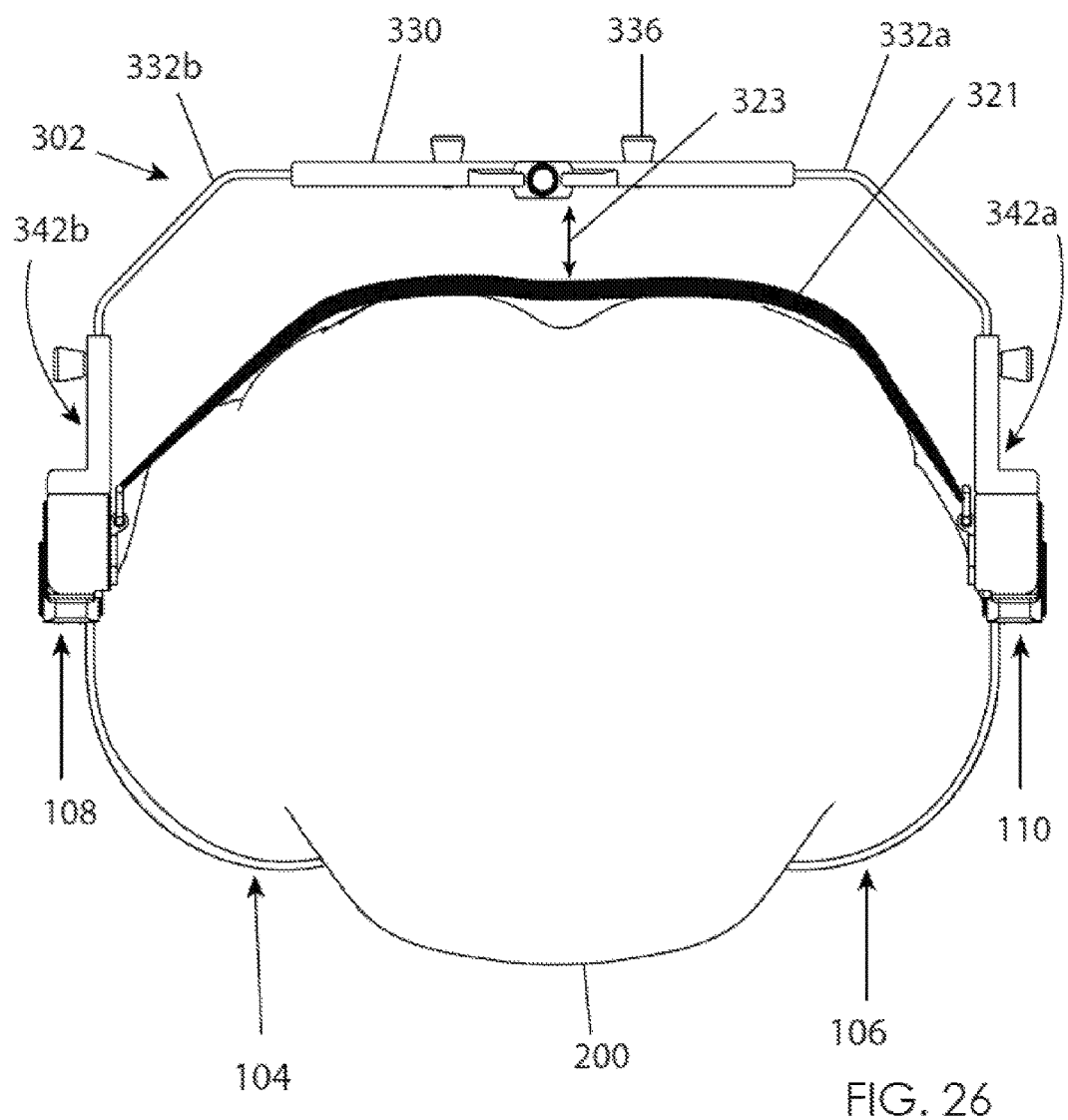
FIG. 26 depicts a top-down view at waist height showing an embodiment of the trunk supporting exoskeleton worn by a person, with a suspension harness coupled to the torque generators.
Figure 27:
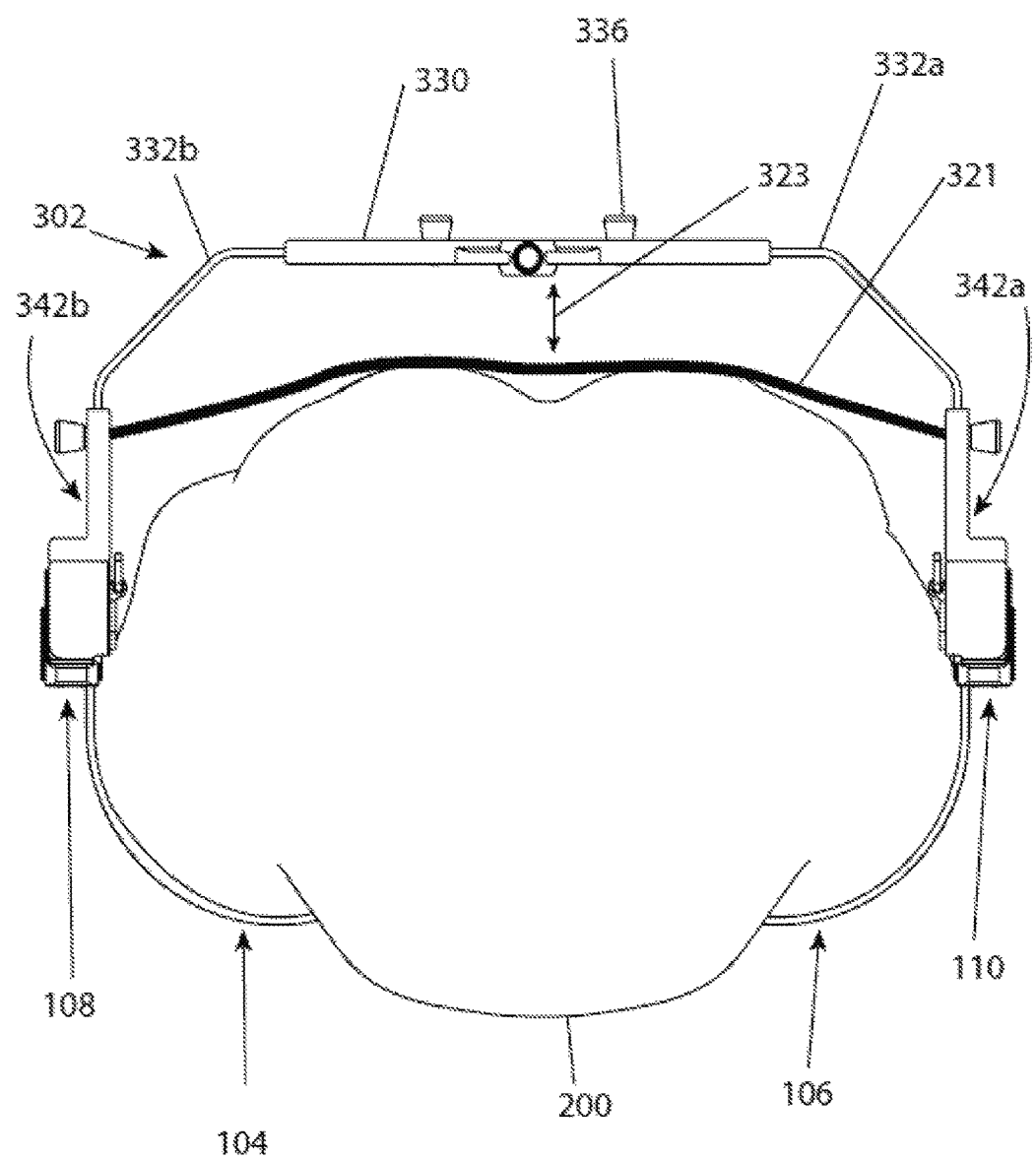
FIG. 27 depicts a top-down view at waist height showing the embodiment of FIG. 27 worn by a person, wherein the suspension harness is coupled to the lower frame.

FIG. 24 shows an embodiment of the invention where supporting trunk 102 further comprises at least one resisting element 316 to provide resistance against the rotational motion 318 of spine frame 304 relative to lower frame 302. In some embodiments of the invention, resisting element 316 is selected from a group consisting of gas springs, leaf springs, tensile springs, compression springs, and combinations thereof. FIG. 25 shows an embodiment of the invention where the resisting element are leaf springs 319a, 319b. In some embodiments of the invention, as shown in FIG. 25, resisting elements 319a, 319b do not resist the rotational motion for a limited range of motion of spine frame 304 relative to lower frame 302. FIG. 26 shows a top view of an embodiment of the invention wherein lower frame 302 comprises a suspension harness 321. Suspension harness 321 is coupled to trunk support exoskeleton 100 on each side of person 200. Suspension harness 321 is configured in such a manner to provide a distance 323 between person 200 and lower frame 302 to prevent contact between person 200 and lower frame 302. As can be seen in FIG. 26, in some embodiments of the invention, suspension harness 321 is coupled to torque generators 108 and 110. As can be seen in FIG. 27, in some embodiments of the invention, suspension harness 321 is coupled to lower frame 302.

Figure 28:
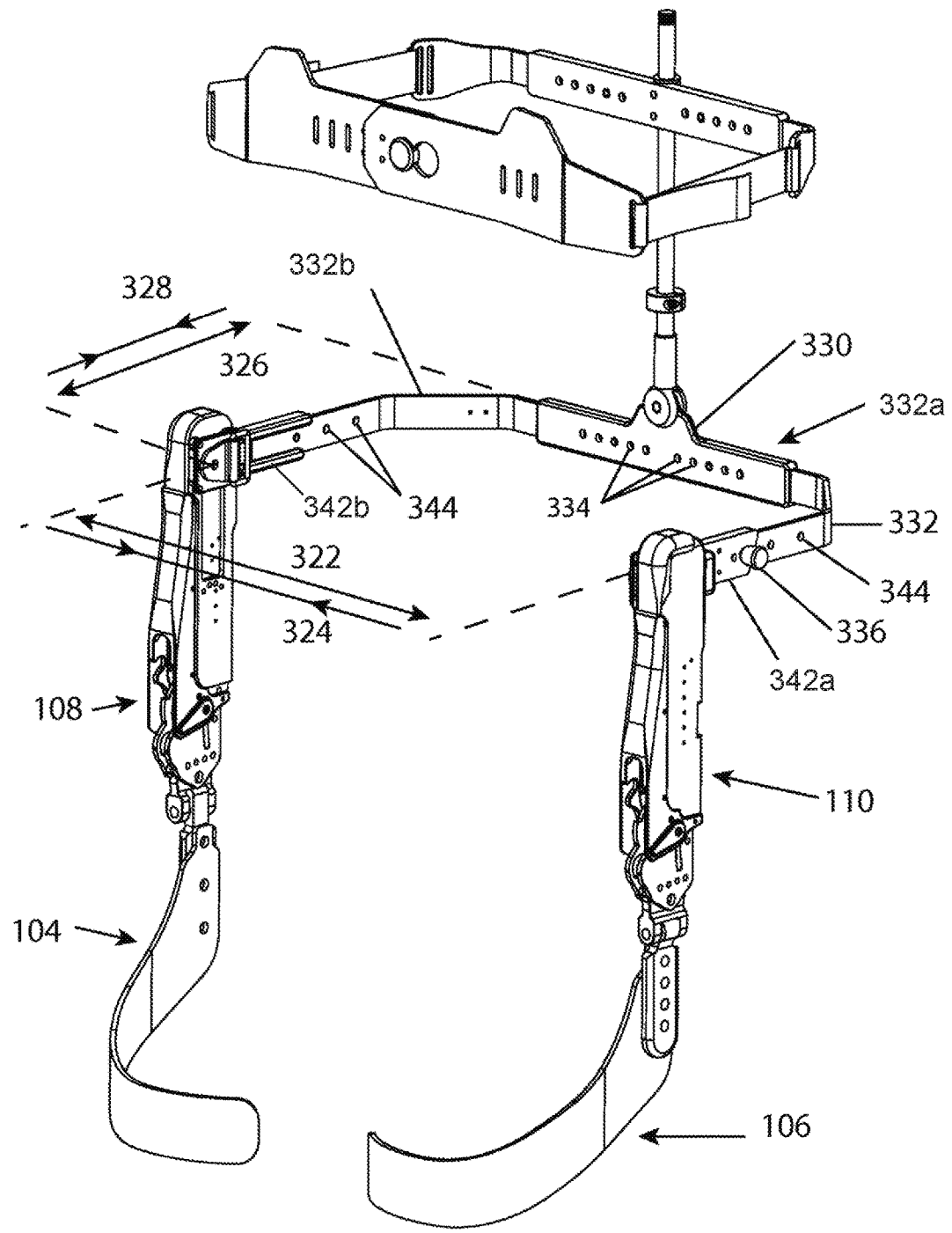
FIG. 28 depicts an anterior three-quarters view showing the trunk supporting exoskeleton of FIG. 21 with the person's body removed for clarity.

FIG. 28 shows an embodiment of the invention wherein lower frame 302 is adjustable in width to fit various people. Arrows 322 and 324 indicate directions of increasing and decreasing width, respectively. In some embodiments, the lower frame 302 is adjustable in depth to fit various people. Arrows 326 and 328 indicate directions of increasing and decreasing depth, respectively. In some embodiments of the invention as shown in FIG. 28, lower frame 302 comprises a lower middle bar 330 and two lower corner bars 332a, 332a. Lower corner bars 332a, 332a can be coupled to lower middle bar 330 at various locations 334 on lower middle bar 330 to provide desirable width adjustment for lower frame 302 to fit various people.

Figure 29:
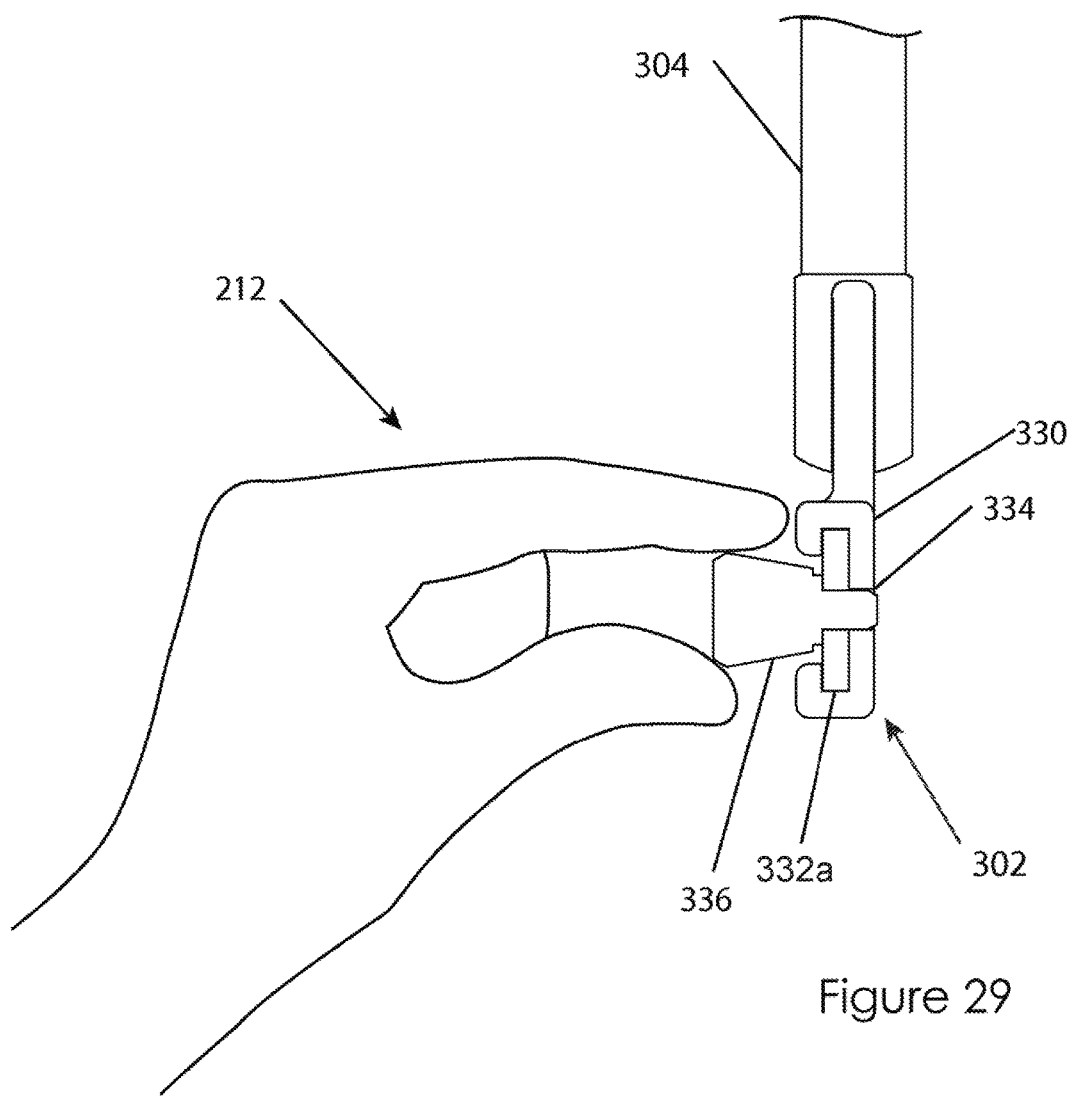
FIG. 29 depicts a cross-sectional view showing an embodiment of the lower frame where lower corner bars are locked by retractable pins.
Figure 30:
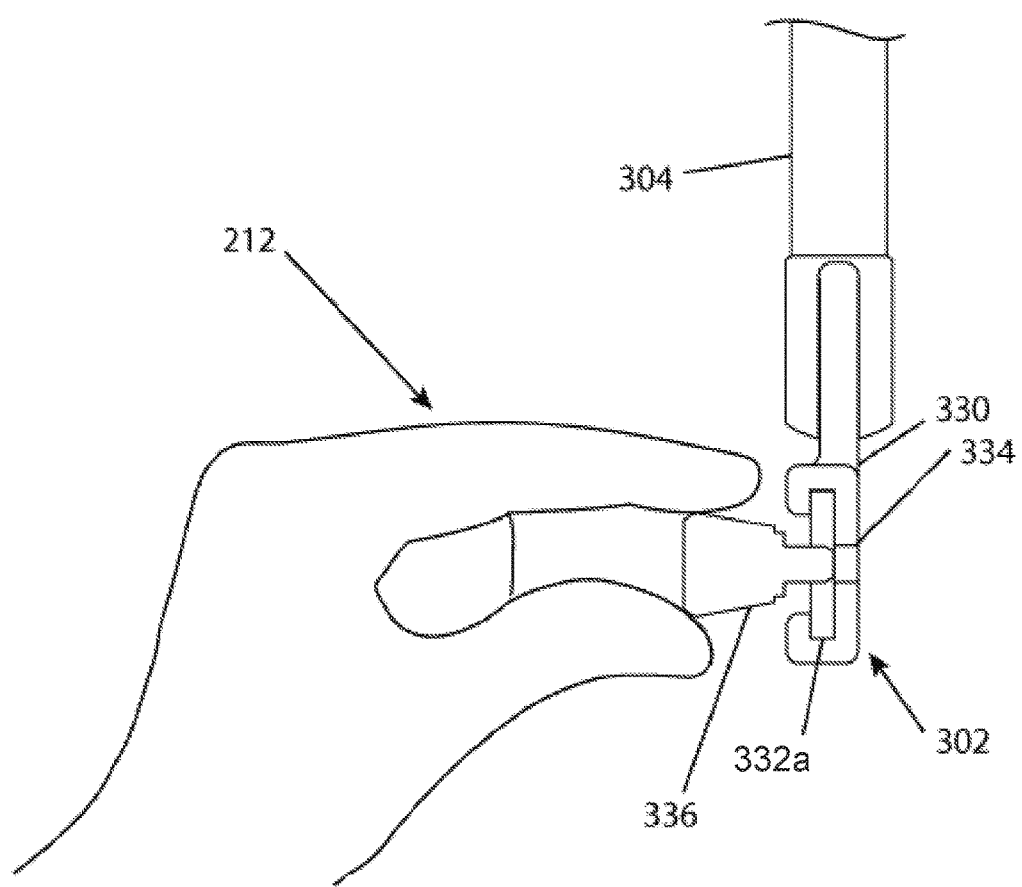
FIG. 30 depicts the embodiment of FIG. 29 where retractable pins have been retracted and lower corner bars are free to slide.

FIGS. 28 and 29 show a cross section of an embodiment of lower frame 302 where hand-retractable pins 336 are used to couple lower corner bars 332a, 332b to lower middle bar 330 at various locations 334. As can be seen in FIG. 29, lower middle bar 330 has a channel cross section and corner bars have rectangular cross sections to provide the sliding motion along arrows 322 and 324 for adjustment. FIG. 29 shows the configuration wherein retractable pin 336 is inserted in lower frame 302. FIG. 30 shows that the retractable pin 336 is retracted from location 334, thus lower corner bars 332a, 332b are free to slide within lower middle bar 330.

Figure 31:
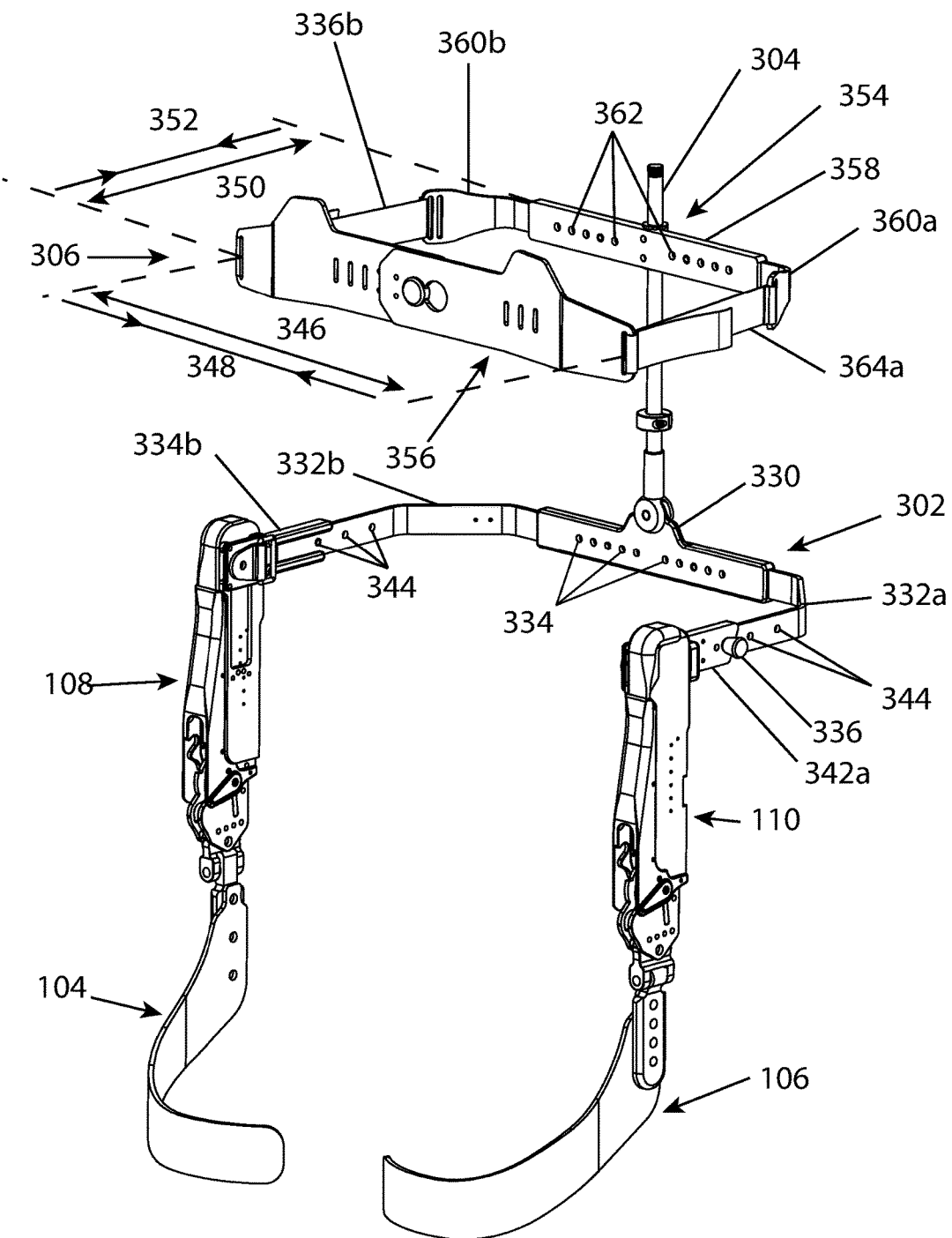
FIG. 31 depicts the trunk supporting exoskeleton of FIG. 28 illustrating upper frame adjustment capability.

In some embodiments of the invention, as illustrated in FIG. 28, lower frame 302 further comprises two opposing side brackets 342a, 342b. Each side bracket 342a, 342b can be coupled to the rest of lower frame 302 at various locations 344 on lower frame 302 to provide desirable depth adjustment for lower frame 302 to fit various people. In some embodiments of the invention, similar to adjustment procedure for width of lower frame, hand-retractable pins 336 have been used to couple respective side bracket 342a, 342b to lower frame 302 at various locations 344. FIG. 31 shows an embodiment of the invention wherein upper frame 306 of supporting trunk 102 is adjustable in width to fit various people. Arrows 346 and 348 indicate directions of increasing and decreasing width, respectively. In some embodiments, upper frame 306 of supporting trunk 102 is adjustable in depth to fit various people. Arrows 350 and 352 indicate directions of increasing and decreasing depth, respectively.

Figure 32:
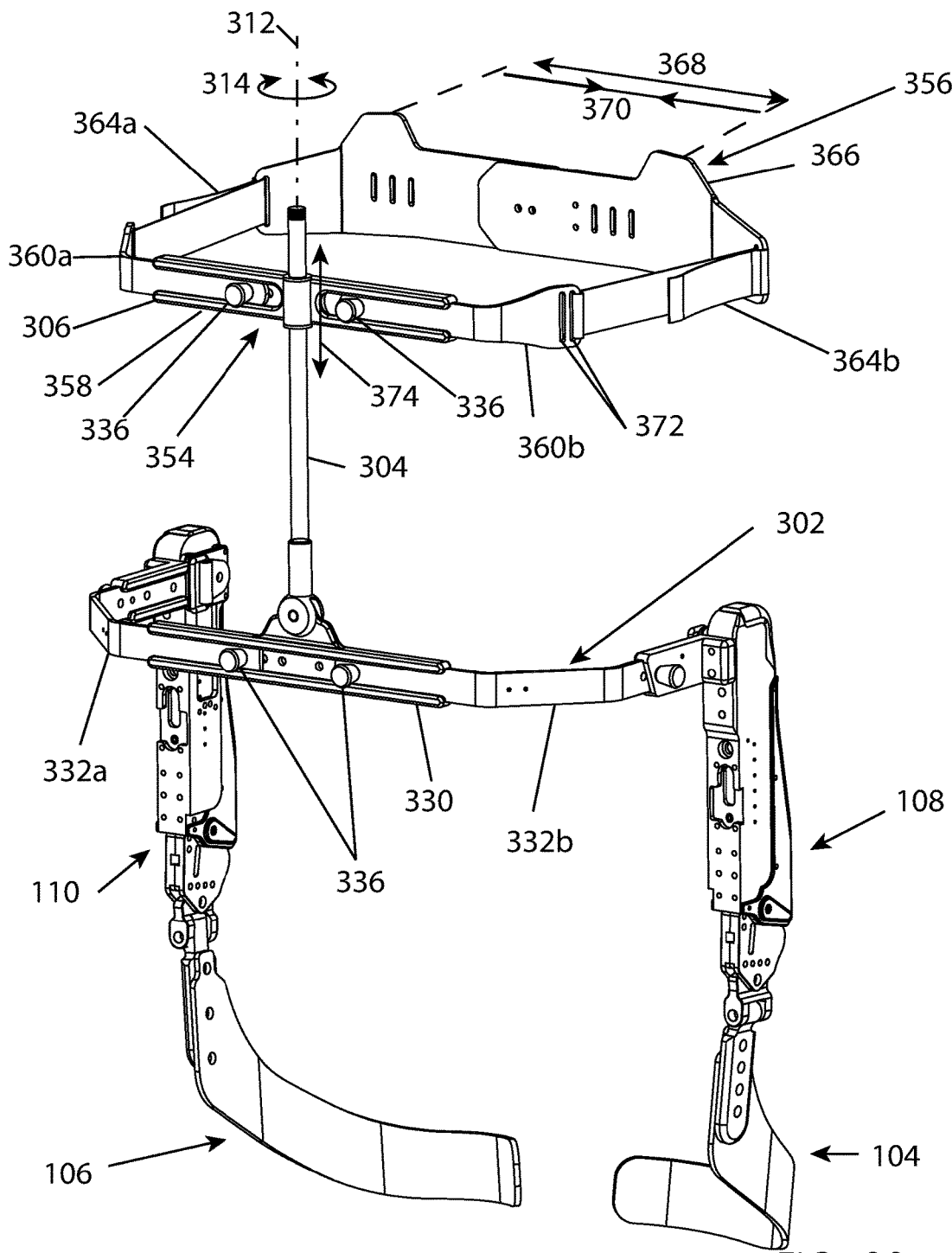
FIG. 32 depicts a posterior three-quarters view of the trunk supporting exoskeleton in FIG. 28 illustrating upper front frame adjustment capability.

Upper frame 306 comprises an upper rear frame 354 coupled to spine frame 304. Upper frame 306 further comprises an upper front frame 356 coupled to upper rear frame 354. Upper front frame 356 is configured to be in contact with the front of said person's trunk 202 such as general area of chest 210 and shoulder 218, as depicted in FIG. 21, for example. In some embodiments of the invention as shown in FIG. 31, upper rear frame 354 comprises an upper middle bar 358 and two upper corner bars 360a, 360b. Upper corner bars 360a, 360b can be coupled to upper middle bar 358 at various locations 362 on upper middle bar 358 to provide desirable width adjustment for upper frame 306 to fit various people. In some embodiments of the invention, as shown in FIG. 32, similar to adjustment procedure for width of lower frame 302, hand-retractable pins 336 have been used to couple upper corner bars 360a, 360b to upper middle bar 358 at various locations 362. In some embodiments of the invention as shown in FIG. 32, upper front frame 356 comprises two connecting members 364a, 364b which are coupled to upper rear frame 354. Upper front frame 356 further comprises at least one chest plate 366 coupled to connecting members 364a, 364b. At least one chest plate 366 is in contact with the front of said person's trunk such as the general area of chest 210 and shoulder 218. Connecting members 364a, 364b can be selected from a group consisting of rigid members, semi-rigid members, straps, adjustable-length strap loops and combinations thereof.

Figure 33:
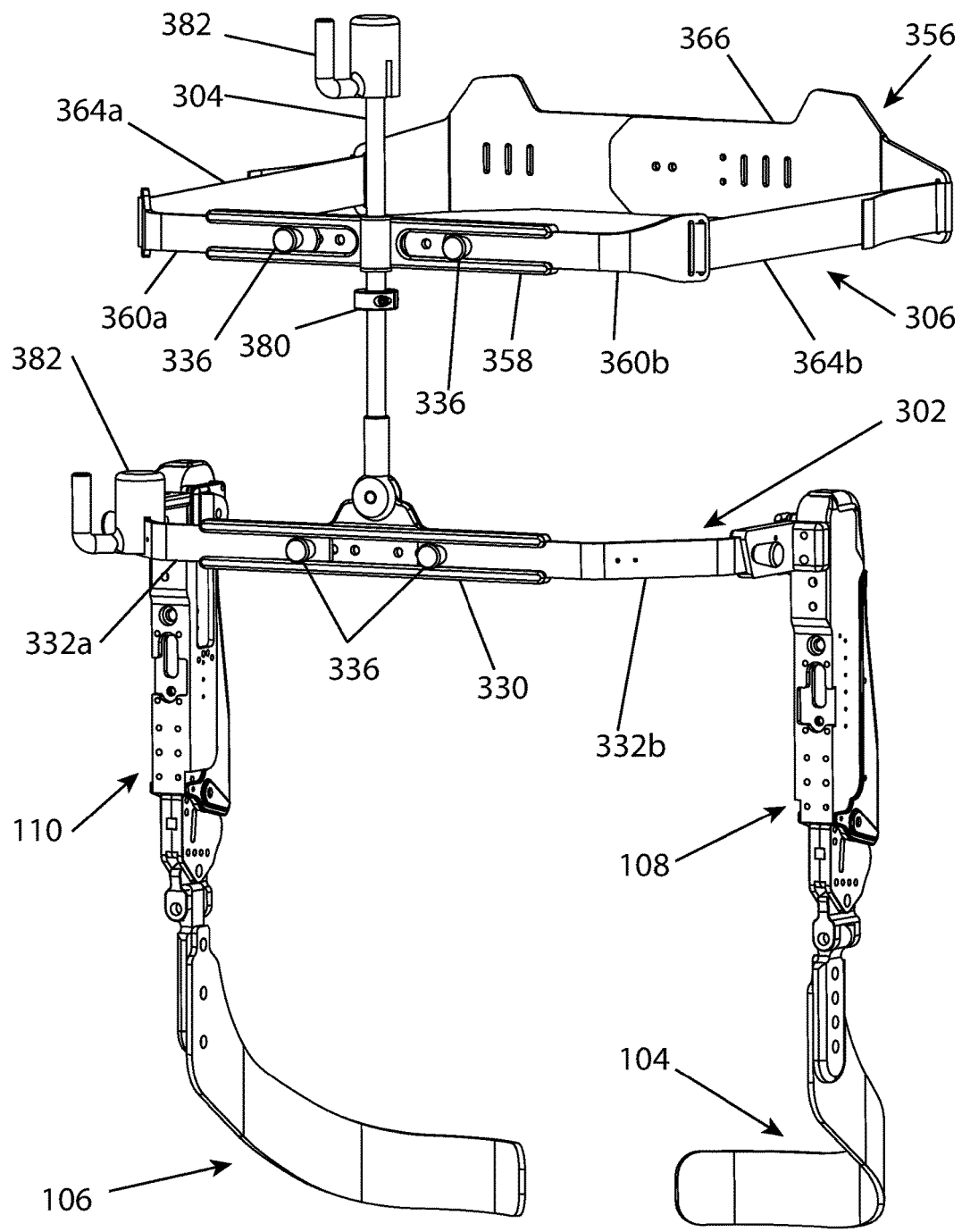
FIG. 33 depicts a posterior three-quarters view of the trunk supporting exoskeleton in FIG. 28 with external objects coupled to the spine frame and lower frame.
Figure 34:
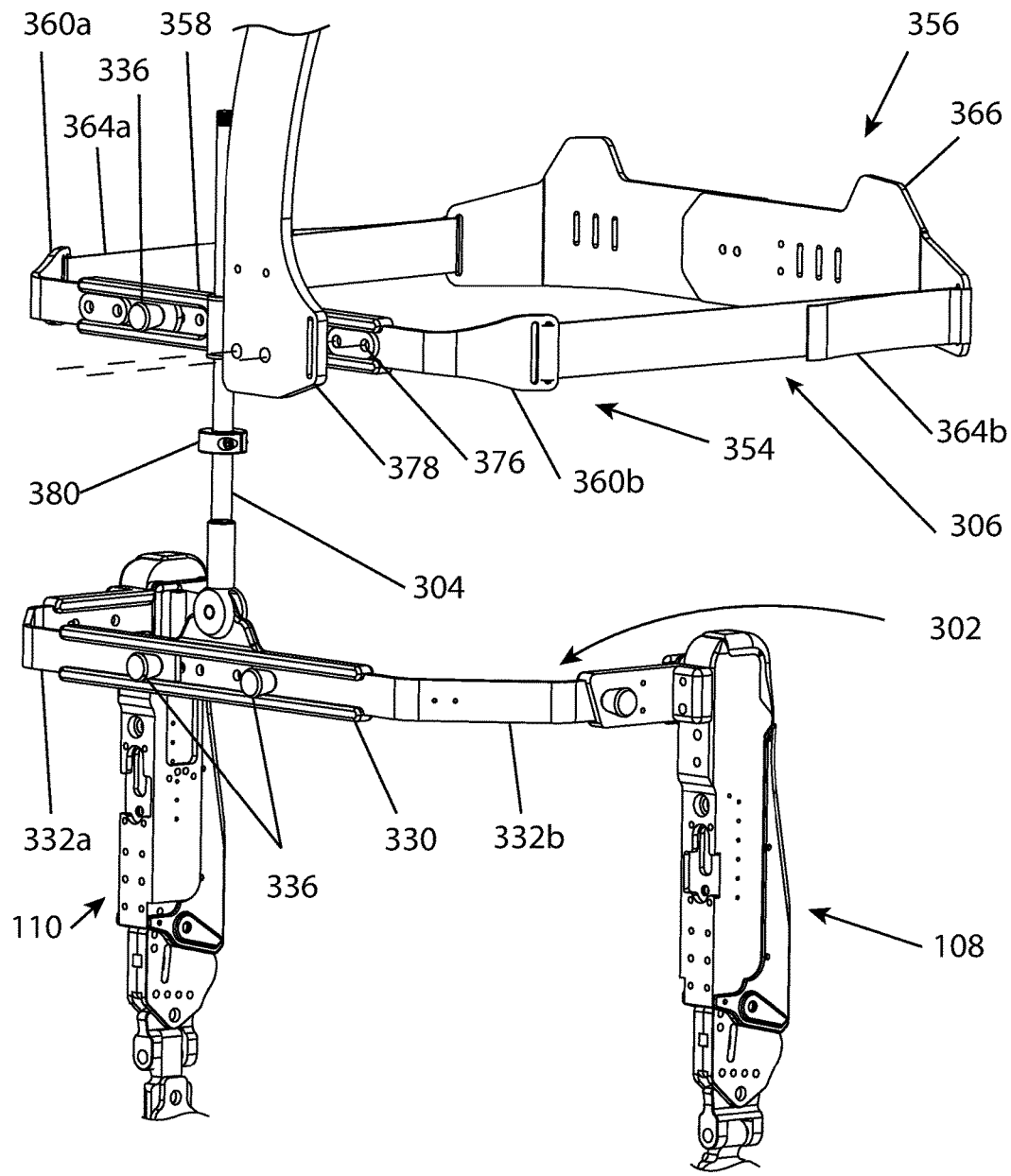
FIG. 34 depicts a posterior three-quarters view of an embodiment of the trunk supporting exoskeleton illustrating attachment of an external object to the upper frame.

FIG. 32 shows an embodiment of the invention in which the width of upper front frame 356 is adjustable to fit various people. Arrows 368 and 370 indicate directions of increasing and decreasing width, respectively. As shown in FIG. 32, in some embodiments of the invention, connecting members 364a, 364b can be coupled to the rest of upper rear frame 354 at various locations 372 to provide desirable depth adjustment for upper frame 306 to fit various people. In the embodiment of FIG. 32, various locations 372 are formed as slots to accommodate connecting elements 364a, 364b (e.g. straps). In some embodiments of the invention, upper frame 306 is configured to slide linearly along spine frame 304. Arrow 374 in FIG. 32 indicates directions of linear sliding motion along spine frame 304. In some embodiments of the invention, as shown in FIG. 32, upper frame 306 is configured to rotate on spine frame 304 along the major axis 312 of spine frame 304. Arrow 314 indicates this rotation. In some embodiments of the invention, trunk supporting exoskeleton 100 can also be employed to carry external objects. In some embodiments, external object holders 382 such as carrying hooks, as shown in FIG. 33, can be mounted on trunk supporting exoskeleton 100 to couple external objects to trunk supporting exoskeleton 100. External object holder 382, as shown in FIG. 33, can be mounted on spine frame 304. External object holder 382 can also be mounted on lower frame 302, also shown in FIG. 33. External objects could be backpack, boxes and other heavy objects. FIG. 34 shows an exploded view of an embodiment of the invention in which an external object 378 can directly be coupled to upper frame 306. In this situation, trunk supporting exoskeleton 100 further comprises a locking element 380 that restricts the sliding movement of upper frame 306 along spine frame 304. FIG. 34 shows an embodiment of upper frame 306 wherein upper corner bars 360a, 360b have several coupling features such as threaded holes 376 for coupling external object 378 to upper frame 306.

Figure 35:
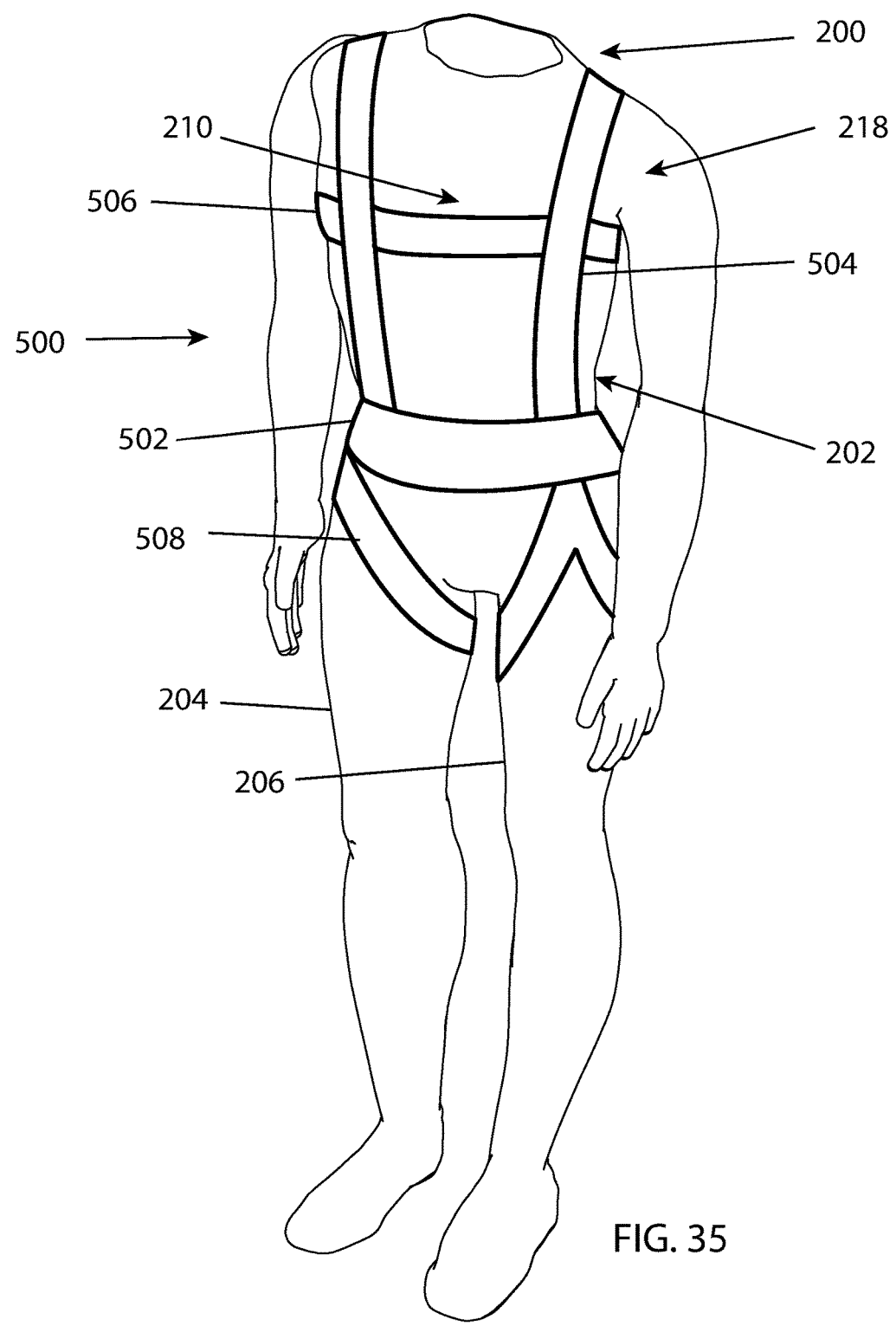
FIG. 35 depicts an anterior three-quarters view of the human machine interface worn by a person.
Figure 36:
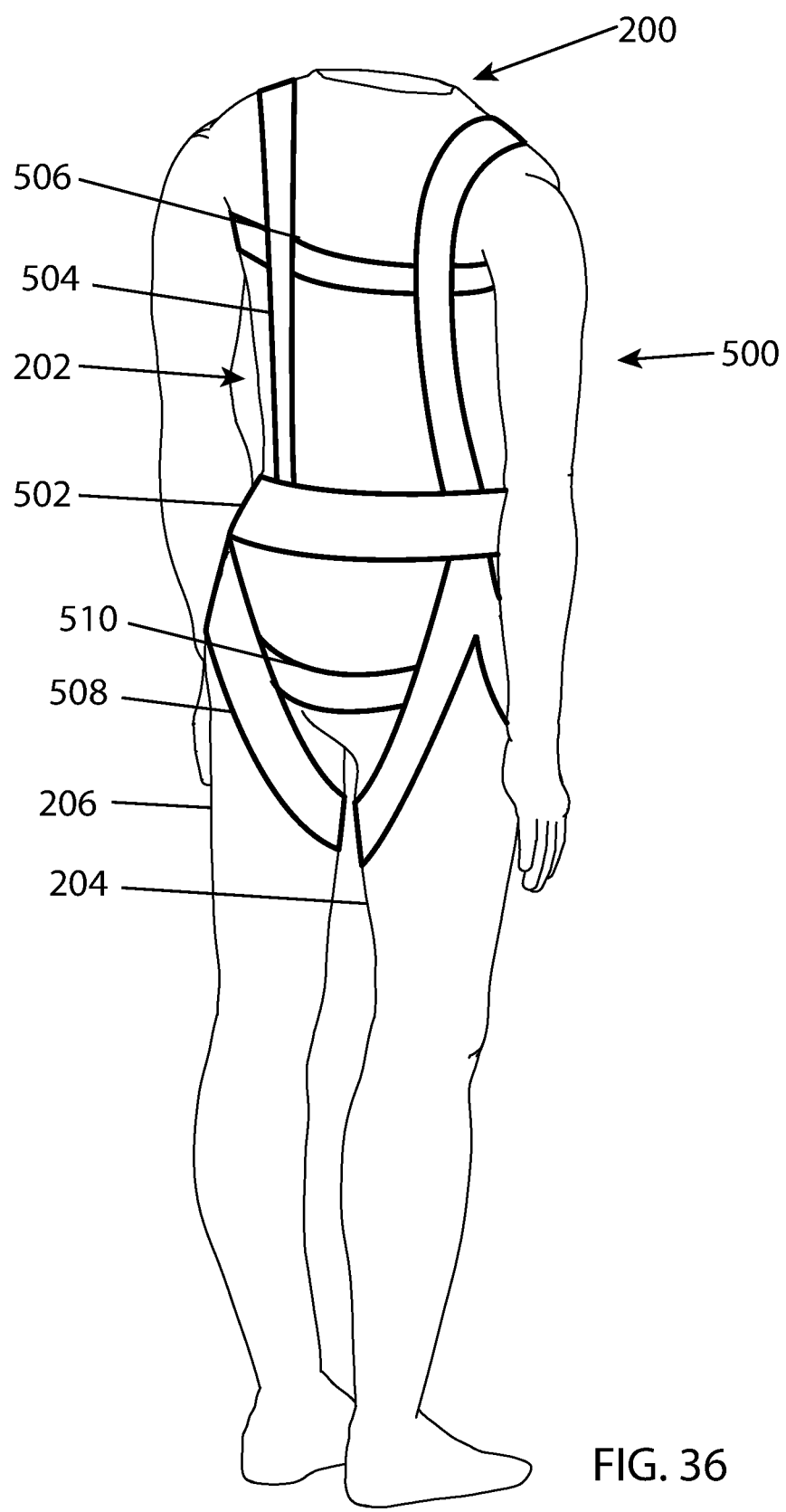
FIG. 36 depicts a posterior three-quarters view of the human machine interface and person of FIG. 35.
Figure 40A:
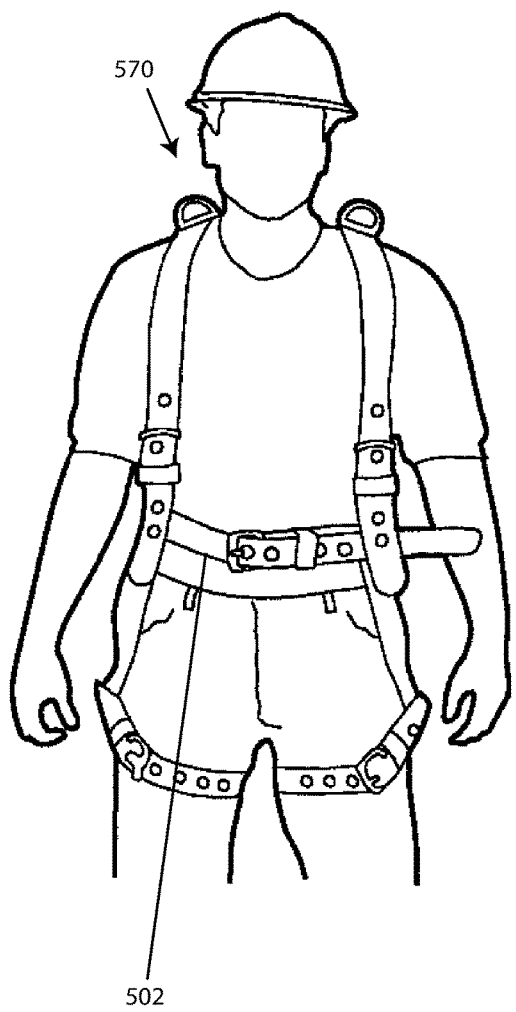
FIGS. 40A and 40B are front and back views of a fall protection safety harness.
Figure 40B:
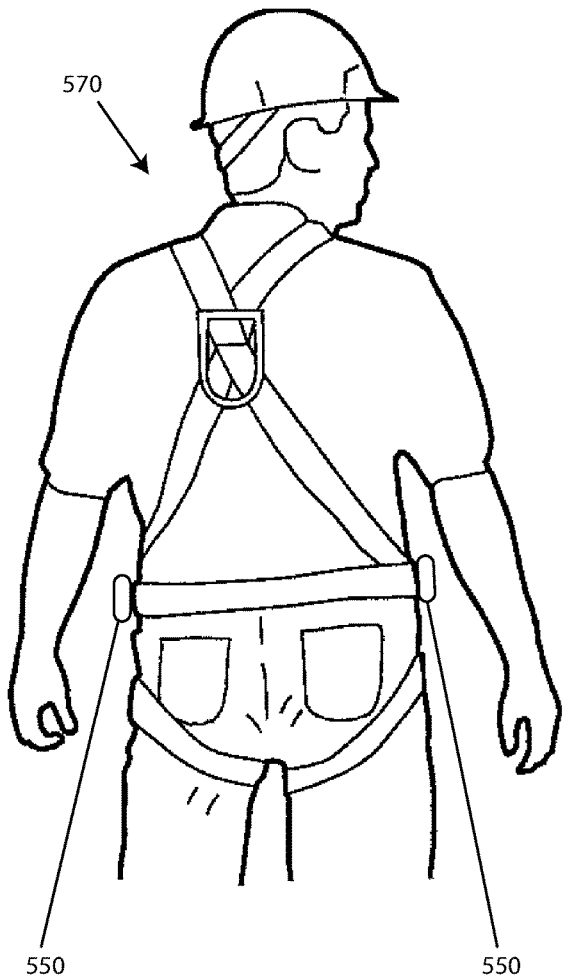

Trunk supporting exoskeleton 100 can be coupled to a human interface system 500 which is configured to be worn by person 200, as depicted in FIG. 35. In some embodiment of the invention, as shown in FIG. 35 and FIG. 36, human interface system 500 comprises a waist belt 502 which is worn on person's waist. In some embodiment of the invention, human interface system 500 comprises two shoulder straps 504 worn on shoulders of person 200. In some embodiment of the invention, human interface system 500 comprises a chest strap 506 worn on the chest of person 200. In some embodiment of the invention, human interface system 500 comprises two thigh straps 508 which are worn around the thighs of person 200. In some embodiment of the invention, human interface system 500 comprises a bridge strap 510 connecting two thigh straps 508 behind person 200. In some embodiment of the invention, human interface system is selected from a group comprising of safety harness, tool belt harness, tool belt, climbing harness, construction worker fall protection safety harness and any combination thereof. In general there are various methods of coupling trunk supporting exoskeleton 100 to human interface system 500. The important issue is to ensure trunk supporting exoskeleton 100 is coupled to human interface system 500 such that trunk supporting exoskeleton 100 robustly stays on person 200 during all kinds of maneuvers. In some embodiment of the invention, torque generators 108 and 110 are configured to be coupled to human interface system 500. In some embodiment of the invention, supporting trunk 102 is configured to be coupled to human interface system 500. In some embodiments of the invention, torque generators 108 and 110 are configured to be coupled to waist belt 502. In some embodiments of the invention, supporting trunk 102 is configured to be coupled to waist belt 502. In some embodiments of the invention, supporting trunk 102 is configured to be coupled to chest strap 506. In some embodiments of the invention, supporting trunk 102 is configured to be coupled to shoulder straps 504. The coupling in all embodiments described above can take place through the use of VELCRO®, buttons, lace, sewing, glue and other coupling mechanisms. In fact in some embodiment of the invention, trunk supporting exoskeleton 100 is configured to be coupled to human interface system 500 through the use of a quick release mechanism 530 depicted in FIG. 37, for example. This is especially useful when trunk support exoskeleton 100 is used with a fall protection safety harness 570 shown in FIGS. 40A and 40B. The trunk support exoskeleton 100 can be coupled to fall protection safety harness 570 through quick release mechanism 530 described below.

Figure 37:
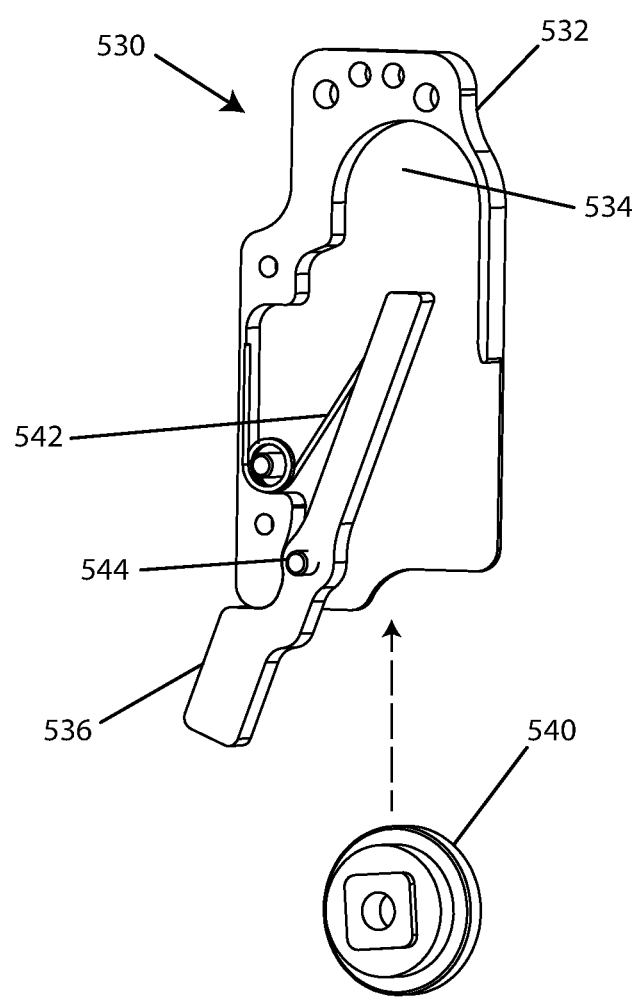
FIG. 37 depicts an embodiment of quick release mechanism in a first position.
Figure 38:
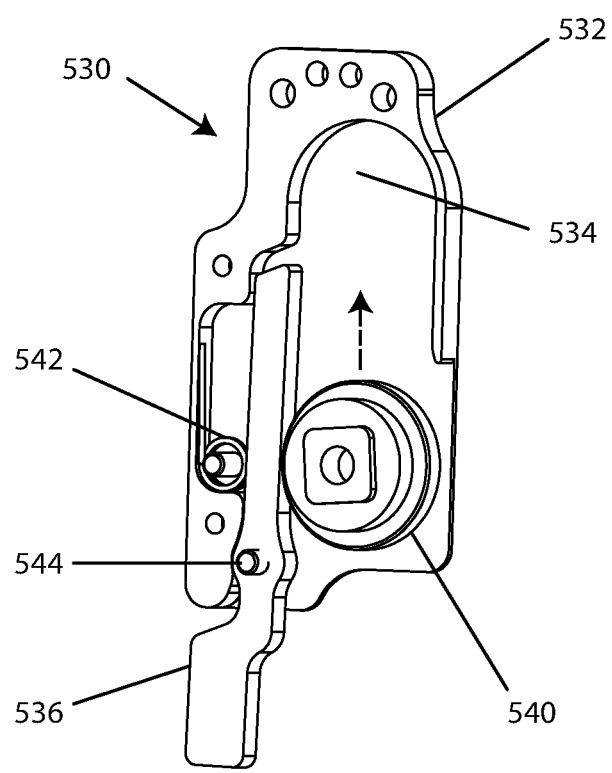
FIG. 38 depicts an embodiment of quick release mechanism in a second position.
Figure 39:
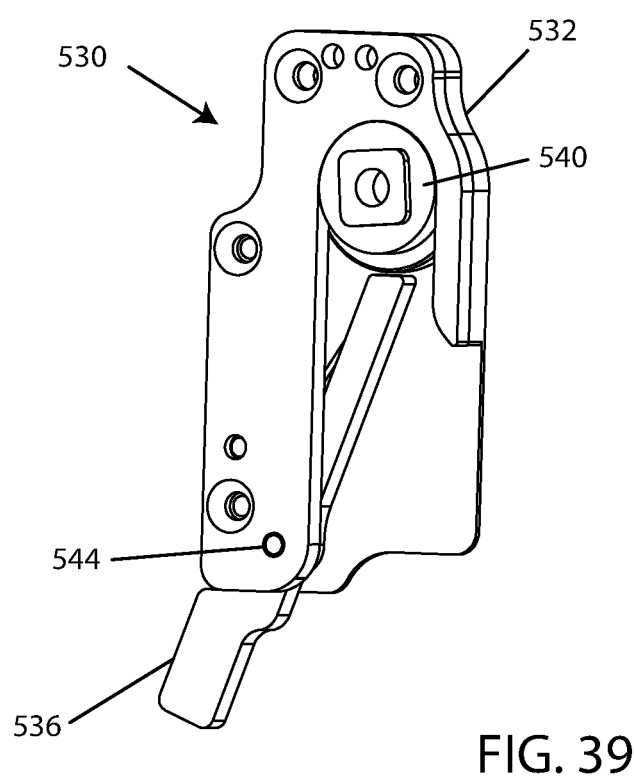
FIG. 39 depicts an embodiment of quick release mechanism in a third, locked position.

FIG. 37 shows an embodiment of the quick release mechanism 530 which is used to couple torque generator 108 or supporting trunk 102 to waist belt 502. Quick release mechanism 530 comprises a holding bracket 532 and a button 540. Holding bracket 532 comprises a cavity 534 formed within holding bracket 532. Holding bracket 532 further comprises an unlocking lever 536, rotatable about a joint 544. Unlocking lever 536 has two positions: locked position and unlocked position. FIG. 38 shows quick release mechanism 530 where unlocking lever 536 is in unlocked position and button 540 is moving toward cavity 534. FIG. 39 shows quick release mechanism 530 where button 540 has moved to its final destination and unlocking lever 536 is in locked position. In some embodiments of the invention, unlocking lever 536 is spring loaded relative to holding bracket 532. This causes the unlocking level positions itself to locked position. FIG. 37 shows an embodiment of the invention where torsional spring 542 brings unlocking lever 536 to its locked position. In operation when button 540 has been placed in cavity 534, button 540 cannot be removed if unlocking lever 536 is in its locked position. However button 540 is free to be removed from cavity 534 if unlocking lever 536 is in its unlocked position. In some embodiments of the invention, button 540 is coupled to waist belt 502 and holding bracket 532 is coupled to trunk supporting exoskeleton 100. In some embodiments of the invention, holding bracket 532 is coupled to waist belt 502 and button 540 is coupled to trunk supporting exoskeleton 100. In some embodiments of the invention, button 540 is coupled to waist belt 502 and holding bracket 532 is coupled to torque generator 108. In some embodiments of the invention, holding bracket 532 is coupled to waist belt 502 and button 540 is coupled to torque generator 108. In some embodiments of the invention, button 540 is coupled to waist belt 502 and holding bracket 532 is coupled to supporting trunk 102. In some embodiments of the invention, holding bracket 532 is coupled to waist belt 502 and button 540 is coupled to supporting trunk 102.

Figure 19:
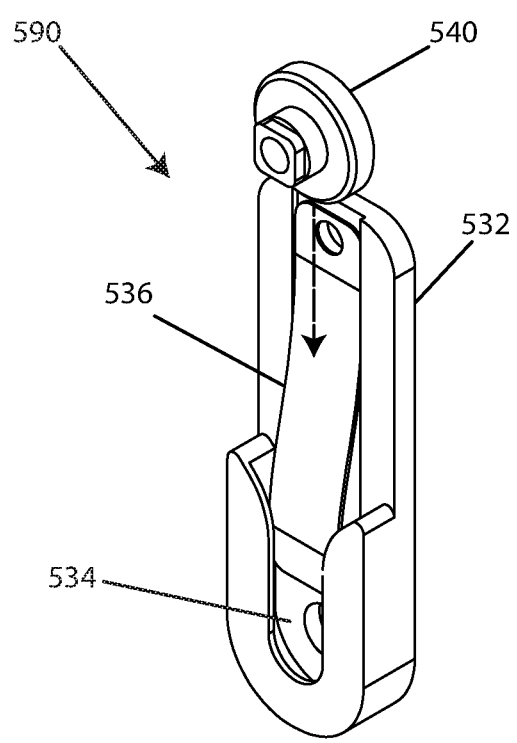
FIG. 19 depicts an embodiment of a quick release mechanism in a first position.
Figure 20:
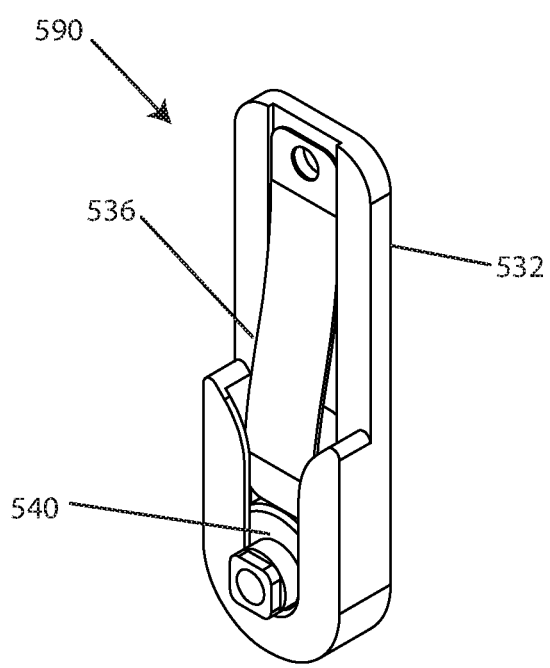
FIG. 20 depicts the quick release mechanism of FIG. 19 in a second locked position.

FIG. 19 shows another embodiment of the quick release mechanism 590 which is used to couple torque generator 108 or supporting trunk 102 to waist belt 502. Quick release mechanism 590 comprises a holding bracket 532 and a button 540. Holding bracket 532 comprises a cavity 534 formed within holding bracket 532. Holding bracket 532 further comprises an unlocking lever 536. Unlocking lever 536 has two positions: locked position and unlocked position. FIG. 19 shows quick release mechanism 590 where button 540 is moving toward cavity 534. FIG. 20 shows quick release mechanism 590 where button 540 has moved to its final destination and unlocking lever 536 is in locked position. In this embodiment unlocking lever 536 is a leaf spring and when it is pushed button 540 can be removed from cavity 534.

Figure 41:
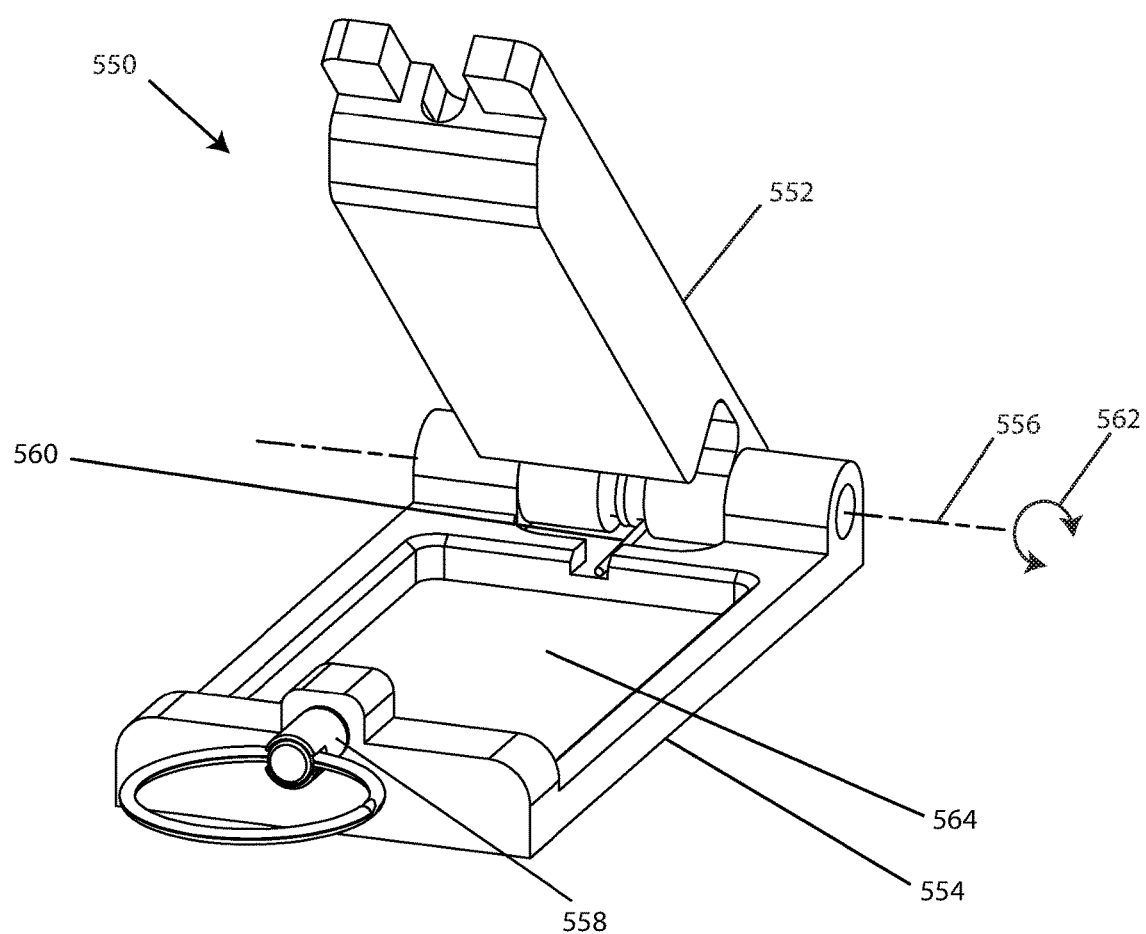
FIG. 41 depicts an embodiment of a coupling device in an open position.
Figure 42:
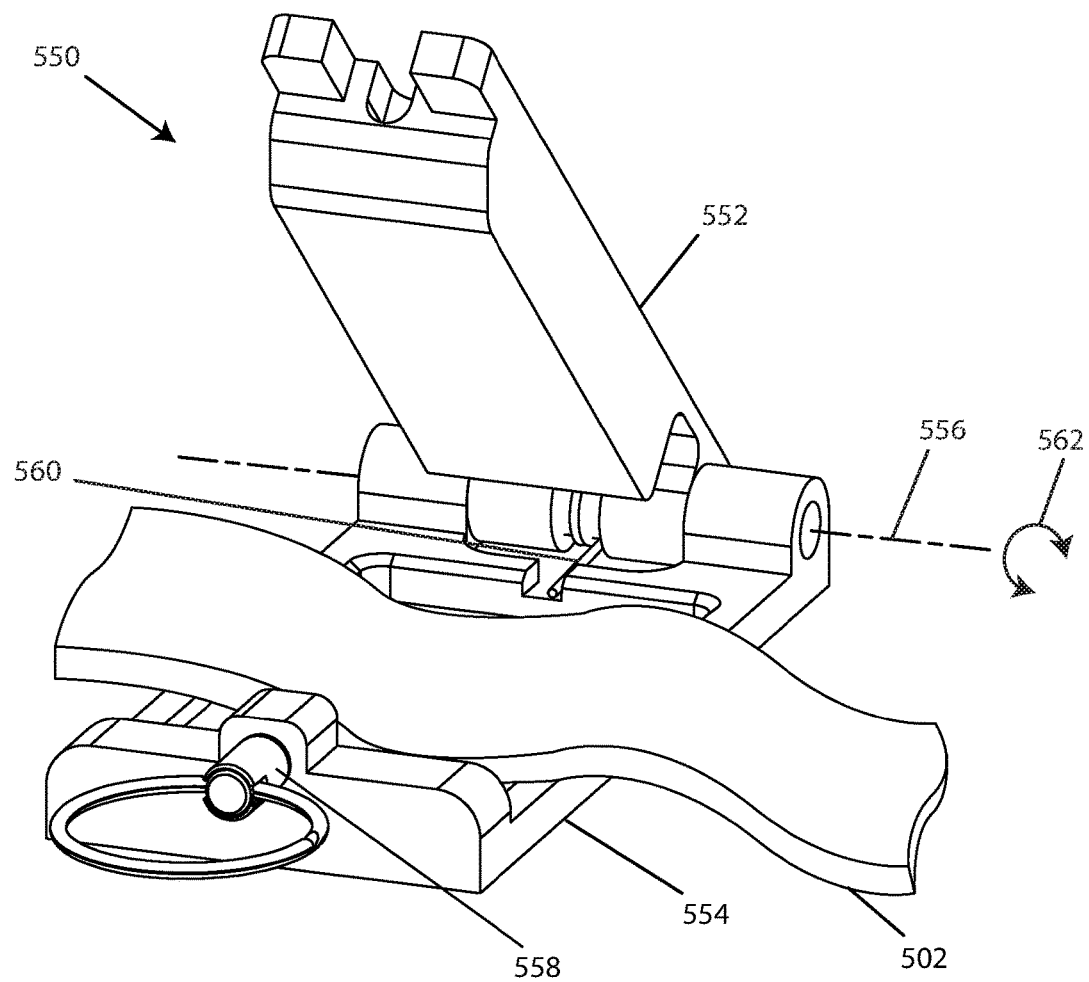
Figure 43:
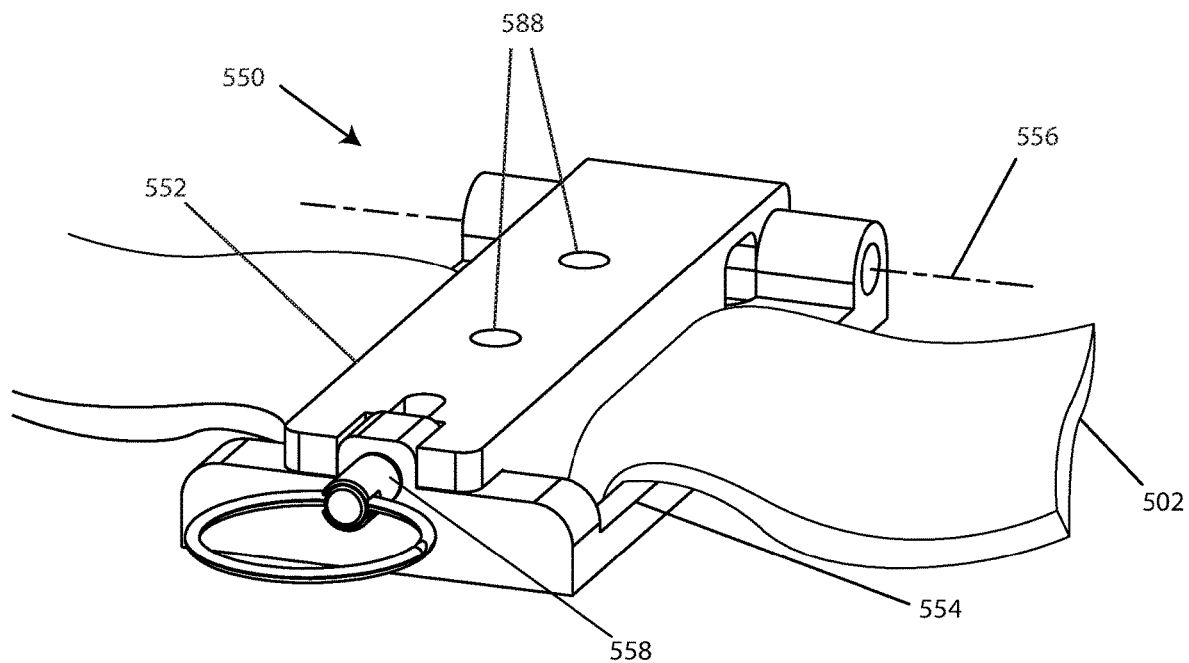
FIG. 43 depicts the coupling device of FIG. 42 in a closed position around the strap.
Figure 44:
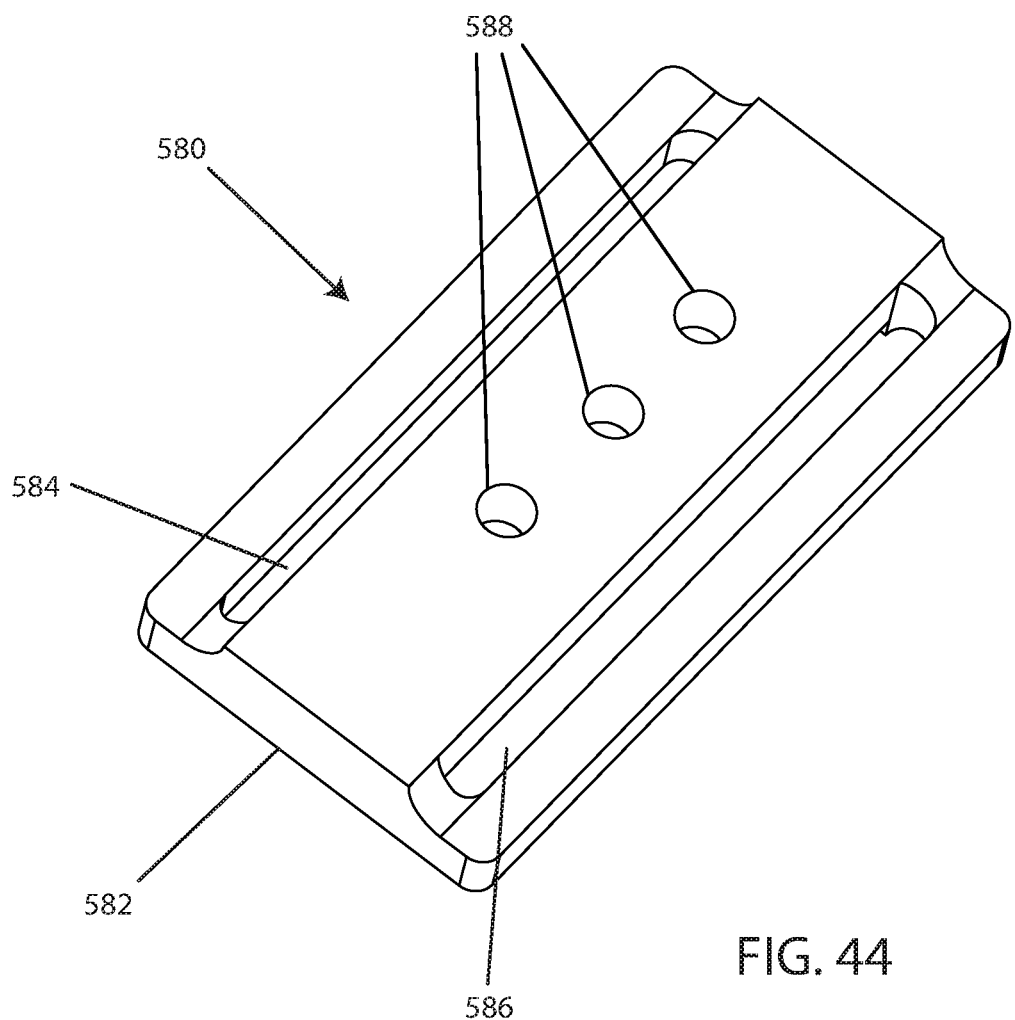
FIG. 44 depicts an embodiment of a coupling device.
Figure 45:
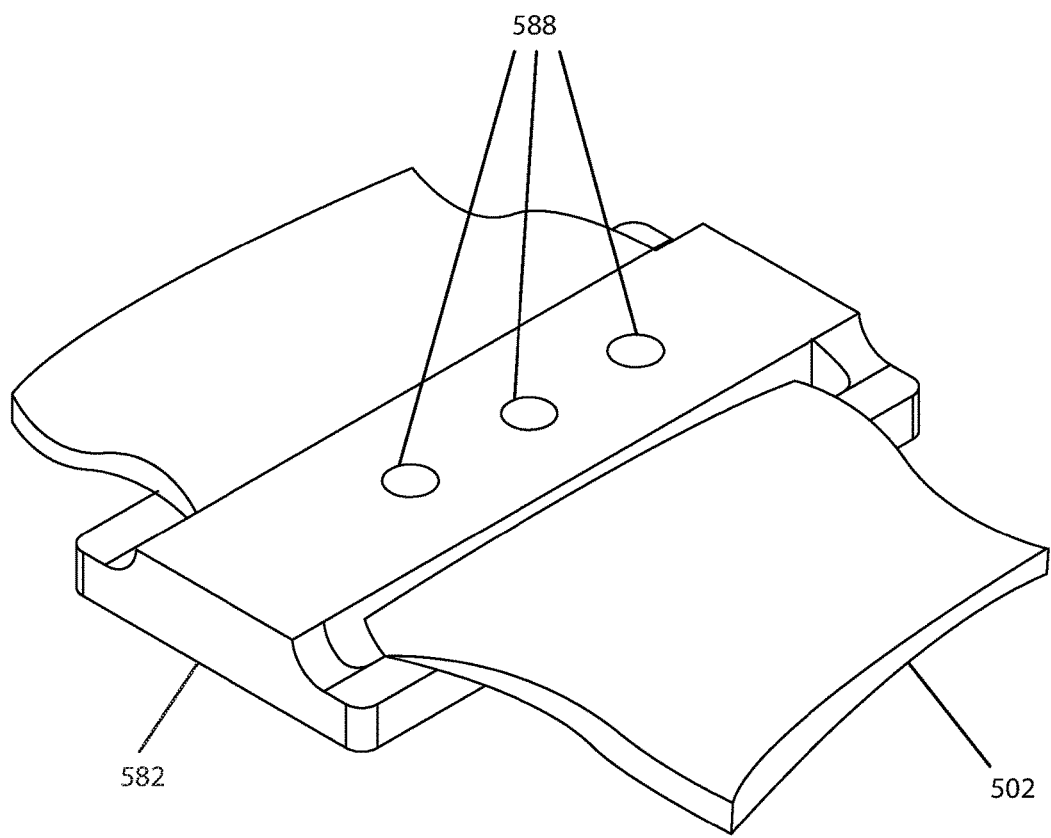

There are many methods of coupling either button 540 or holding bracket 532 to waist belt 502 of human interface system 500 or fall protection safety harness 570. FIG. 41 shows an embodiment of a coupling device 550 that allows for such a safe coupling of button 540 or holding bracket 532 to any waist belt 502 of human interface system 500 or fall protection safety harness 570. Clamping device 550 comprises an outer plate 552 which is configured to be coupled to exoskeleton and in inner plate 554. Outer plate 552 has interface or coupling features such as threaded holes 588 to couple to a holding bracket 532 or a button 504, as shown in FIG. 43. In some embodiments of invention inner plate 554 comprises cavity 564 to allow the belt to curve. In operation when inner plate 554 and outer plate 552 are pushed against each other, waist belt 502 is clamped between inner plate 554 and outer plate 552. In some embodiments of invention, inner plate 554 and outer plate 552 rotate relative to each other along axis 556. Arrow 562 shows the direction of motion inner plate 554 and outer plate 552 relative to each other. In some embodiments of invention, a torsion spring 560 can be used to keep two inner plate 554 and outer plate 552 either open or closed relative to each other. FIG. 42 shows the configuration where two inner plate 554 and outer plate 552 are in open position. FIG. 43 shows the situation where waist belt 502 of human interface system 500 or fall protection safety harness 570 is clamped in clamping device 550. Outer plate 552 has interface features such as threaded holes 588 to couple to a holding bracket 532 or a button 504. Spring plunger 558 is used to lock and release outer plate 552 from its clamping position. When spring plunger 558 is pulled out plate 552 gets released. In some embodiments of invention, inner plate 554 and said outer plate 552 are pushed against each other by use of fasteners. FIG. 40 shows an embodiment where clamping device 550 is employed to couple an exoskeleton to fall protection safety harness 570. FIGS. 44 and 45 show another embodiment of coupling device 580 to couple an exoskeleton to a waist belt 502 worn by a person. Coupling device 580 comprises a block 582. Block 582 comprises two openings 584 and 586. When waist belt 502 passes through two openings 584 and 586, waist belt 502 is secured to block 582. Coupling features 588 are used to couple block 582 to an exoskeleton.

Figure 18:
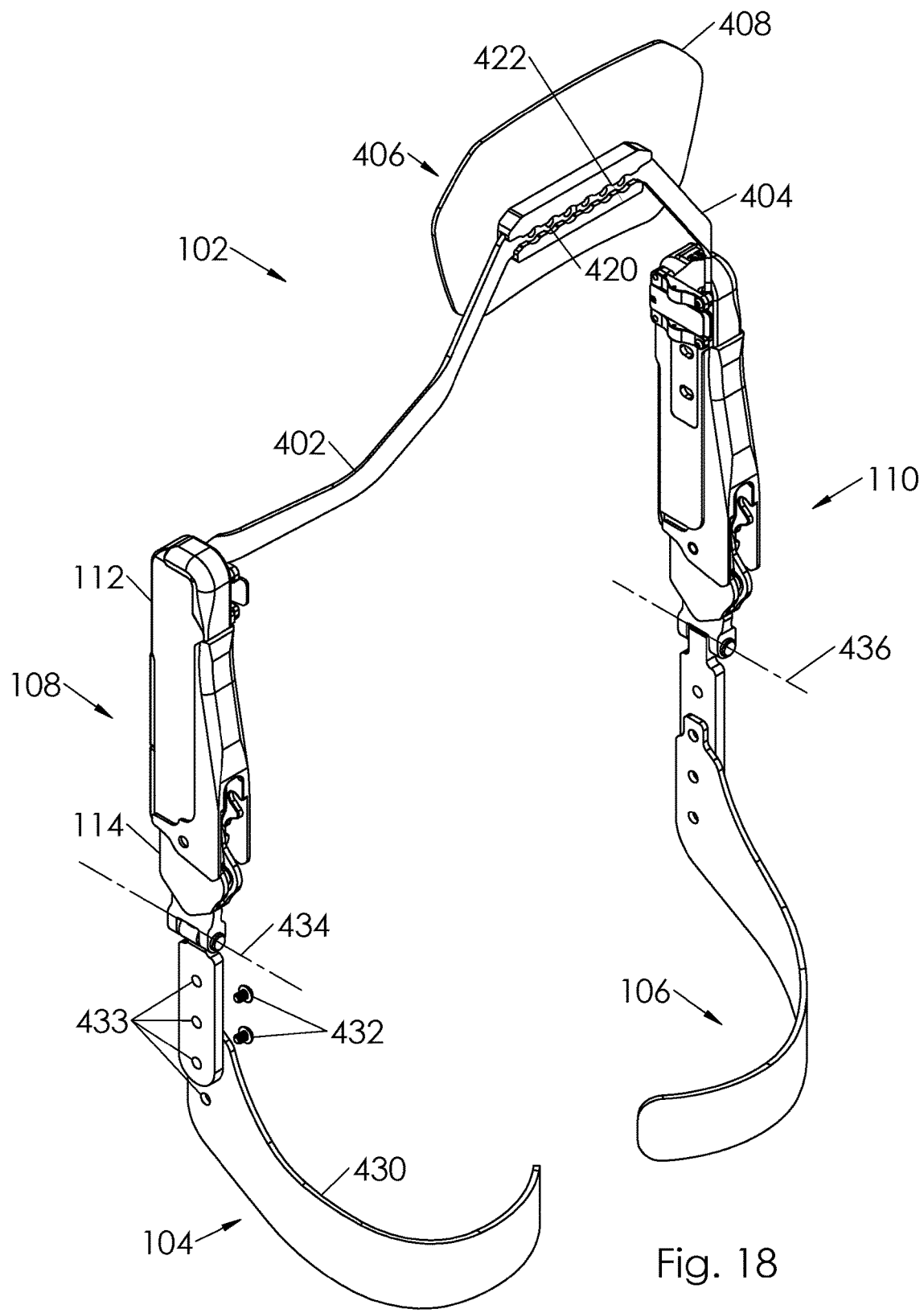
FIG. 18 is a back perspective view of an embodiment of a supporting trunk of the present invention including a means for adjusting thigh braces.

In some embodiments of the invention, as shown in FIG. 18, thigh links 104 and 106 further comprise two rotary abduction-adduction axes 434 and 436. Since thigh links 104 and 106 are mirrored, only thigh link 104 is described here. As shown in FIG. 18, thigh links 104 and 106 are able to rotate along axes 434 and 436. In some embodiment of the invention, thigh links 104 comprises at least one thigh brace 430 configured to couple to person's thigh. Thigh brace 430 comprises any material or combination of materials capable of performing the indicated functions. Examples of materials of thigh brace 430 includes, without limitation, fabric materials, plastic materials, leather materials, carbon fiber materials, metallic materials, and combinations thereof. In some embodiment of the invention, thigh links 104 and 106 are adjustable in length for to fit various users. As shown in FIG. 18, in some embodiments of the invention, thigh holes 433 and fasteners 432 are used to adjust the location of thigh brace 430.

What is claimed is:

1. A trunk supporting exoskeleton configured to be worn by a person to reduce muscle forces in a back of the person during forward lumbar flexion, said trunk supporting exoskeleton comprising:
    a supporting trunk configured to be coupled to a trunk of the person;
    first and second thigh links configured to move in unison with thighs of the person in manner resulting in flexion and extension of the first and second thigh links relative to said supporting trunk; and
    first and second torque generators configured to be located on both left and right halves of said person substantially close to a hip of the person, coupling said supporting trunk to said first and second thigh links respectively and configured to generate torque between said first and second thigh links and said supporting trunk, wherein:
        when said person bends forward in a sagittal plane such that a predetermined portion of said supporting trunk passes beyond a predetermined angle from vertical, at least one of said first and second torque generators imposes a resisting torque between said supporting trunk and at least one of the first and second thigh links, causing said supporting trunk to impose a force against the trunk of the person and at least one of said first and second thigh links to impose a force onto at least one of the thighs of the person and,
        when said predetermined portion of said supporting trunk does not pass beyond said predetermined angle from vertical, said first and second torque generators, through an entire range of motion of said first and second thigh links, impose no resisting torques between said supporting trunk and said respective first and second thigh links.

2. The trunk supporting exoskeleton of claim 1, wherein at least one of said first and second torque generators comprises:
    an upper bracket configured to be coupled to said supporting trunk;
    a lower bracket configured to be coupled to one of the first and second thigh links and rotatably coupled to said upper bracket;
    a pendulum rotatably coupled to said upper bracket;
    an engagement bracket slidingly coupled to said upper bracket; and
    a compression spring comprising a first end and second end, the first end rotatably coupled to said lower bracket, the second end rotatably coupled to said engagement bracket;
    wherein when said predetermined portion of said supporting trunk extends beyond said predetermined angle from vertical, said pendulum comes into contact with said engagement bracket and prevents it from sliding, causing said compression spring to provide a resisting torque between said upper bracket and said lower bracket, and
    wherein when said predetermined portion of the supporting trunk does not extend beyond said predetermined angle from vertical, said pendulum is not in contact with said engagement bracket, said engagement bracket is free to slide on said upper bracket, and said compression spring does not provide the resisting torque between said upper bracket and said lower bracket.

3. The trunk supporting exoskeleton of claim 2, wherein said engagement bracket further comprises teeth positioned on one side of the engagement bracket to engage with said pendulum.

4. The trunk supporting exoskeleton of claim 2, further comprising an angle adjustment mechanism coupled to the upper bracket and configured to adjust said predetermined angle.

5. The trunk supporting exoskeleton of claim 4,
    wherein said pendulum is magnetic,
    wherein said angle adjustment mechanism further comprises a magnetic adjustment screw located in an adjustment screw hole on said upper bracket in close proximity of said pendulum, and
    wherein when said magnetic adjustment screw is turned to change position relative to said pendulum, said predetermined angle from vertical changes.

6. The trunk supporting exoskeleton of claim 2, further comprising an override mechanism coupled to the upper bracket and configured to prevent said pendulum from engaging said engagement bracket.

7. The trunk supporting exoskeleton of claim 6,
    wherein said pendulum is magnetic,
    wherein said override mechanism comprises:
        an override slider configured to slide on said upper bracket; and
        an override magnet coupled to said override slider,
    wherein, when said override slider is in an override position, said override magnet retracts said pendulum and prevents said pendulum from contacting said engagement bracket, and
    wherein, when said override slider is in a non-override position, said override magnet does not retract said pendulum, allowing said pendulum to come into contact with said engagement bracket when a predetermined portion of said upper bracket passes beyond said predetermined angle from vertical.

8. The trunk supporting exoskeleton of claim 2, wherein the compression spring in said lower bracket is adjustable to change levels of the resisting torque.

9. The trunk supporting exoskeleton of claim 8,
    wherein said lower bracket comprises a channel and a sliding block,
    wherein the sliding block is rotatably coupled to said first end of said compression spring and is configured to have different positions in said channel, and
    wherein the different positions of said sliding block in said channel corresponds to different positions of said compression spring relative to an exoskeleton joint between the upper bracket and the lower bracket to change levels of the resisting torque.

10. The trunk supporting exoskeleton of claim 1,
wherein said supporting trunk comprises two side brackets coupled to said first and second torque generators, and
wherein said supporting trunk comprises a chest plate configured to contact the trunk of the person in a chest area of the person.

11. The trunk supporting exoskeleton of claim 1, wherein location of said supporting trunk relative to said first and second torque generators is adjustable.

12. The trunk supporting exoskeleton of claim 1, wherein a width of said trunk supporting exoskeleton is adjustable by adjusting a distance between said first and second torque generators through adjusting a width of said supporting trunk.

13. The trunk supporting exoskeleton of claim 1, wherein said supporting trunk comprises:
a lower frame configured to locate behind said person and configured to partially surround the trunk of the person, the lower frame coupled to said first and second torque generators;
a spine frame configured to locate behind said person and rotatably coupled to said lower frame; and
an upper frame coupled to said spine frame and configured to be in contact with the trunk of the person.

14. The trunk supporting exoskeleton of claim 13, wherein said spine frame is configured to bend laterally relative to said lower frame.

15. The trunk supporting exoskeleton of claim 13, wherein said spine frame is configured to rotate relative to said lower frame, along an axis substantially parallel to a cranial-caudal axis of the person.

16. The trunk supporting exoskeleton of claim 13, wherein said supporting trunk further comprises at least one resisting element configured to provide resistance against rotational motion of said spine frame relative to said lower frame.

17. The trunk supporting exoskeleton of claim 13,
wherein said lower frame comprises a suspension harness coupled to said trunk supporting exoskeleton,
wherein said suspension harness is configured to provide a distance between said person and said lower frame to prevent contact between said person and said lower frame.

18. The trunk supporting exoskeleton of claim 17, wherein said lower frame is size adjustable.

19. The trunk supporting exoskeleton of claim 13, where the upper frame is size adjustable.

20. The trunk supporting exoskeleton of claim 13, wherein said upper frame is configured to move relative to said spine frame.

21. The trunk supporting exoskeleton of claim 1, wherein said trunk supporting exoskeleton is configured to couple to a human interface system configured to be worn by said person.

22. The trunk supporting exoskeleton of claim 21, wherein said human interface system comprises a waist belt configured to be worn on a waist of said person.

23. The trunk supporting exoskeleton of claim 22, wherein said first and second torque generators are configured to be coupled to said waist belt.

24. The trunk supporting exoskeleton of claim 22,
wherein said trunk supporting exoskeleton is configured to be coupled to said waist belt through a quick release mechanism,
wherein said quick release mechanism comprises:
a button;
a holding bracket comprising a cavity formed within said holding bracket; and
an unlocking lever having two positions;
wherein when said button has been placed in said cavity, said button cannot be removed if said unlocking lever is in a first position, and
wherein, when said button has been placed in said cavity, said button is free to be removed from said cavity if said unlocking lever is in a second position.

25. The trunk supporting exoskeleton of claim 21, wherein said human interface system comprises two shoulder straps configured to be worn on shoulders of said person.

26. The trunk supporting exoskeleton of claim 21, wherein said human interface system comprises two thigh straps configured to be worn around thighs of said person.

27. The trunk supporting exoskeleton of claim 21, wherein said human interface system is selected from a group comprising of a safety harness, a tool belt harness, a tool belt, a climbing harness, a construction worker fall protection safety harness, and any combination thereof.

* * * * *

UNITED STATES PATENT AND TRADEMARK OFFICE
CERTIFICATE OF CORRECTION

| | | |
|---|---|---|
| PATENT NO. | : 9,744,066 B2 | Page 1 of 1 |
| APPLICATION NO. | : 14/944635 | |
| DATED | : August 29, 2017 | |
| INVENTOR(S) | : Homayoon Kazerooni et al. | |

It is certified that error appears in the above-identified patent and that said Letters Patent is hereby corrected as shown below:

Please change the "Government License Rights" section to the following:
Government License Rights
This invention was made with government support under Grant No. 1317978 and Grant No. 1456369 awarded by the National Science Foundation (NSF). The government has certain rights in the invention.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*